US012790586B2

(12) United States Patent
Hiramine et al.

(10) Patent No.: US 12,790,586 B2
(45) Date of Patent: Nov. 10, 2026

(54) BRAIN ORGANOID AND USE THEREOF

(71) Applicants: JSR Corporation, Minato-ku (JP); KEIO UNIVERSITY, Minato-ku (JP)

(72) Inventors: Hayato Hiramine, Tokyo (JP); Hideyuki Okano, Tokyo (JP); Seiji Shiozawa, Tokyo (JP); Mitsuru Ishikawa, Tokyo (JP)

(73) Assignees: JSR Corporation, Minato-ku (JP); KEIO UNIVERSITY, Minato-ku (JP)

( * ) Notice: Subject to any disclaimer, the term of this patent is extended or adjusted under 35 U.S.C. 154(b) by 1052 days.

(21) Appl. No.: 17/773,784

(22) PCT Filed: Nov. 5, 2020

(86) PCT No.: PCT/JP2020/041351

§ 371 (c)(1),
(2) Date: May 2, 2022

(87) PCT Pub. No.: WO2021/090877

PCT Pub. Date: May 14, 2021

(65) Prior Publication Data

US 2022/0380725 A1 Dec. 1, 2022

(30) Foreign Application Priority Data

Nov. 6, 2019 (JP) ................................ 2019-201231

(51) Int. Cl.
*C12N 5/079* (2010.01)
*G01N 33/50* (2006.01)

(52) U.S. Cl.
CPC ....... *C12N 5/0618* (2013.01); *G01N 33/5082* (2013.01); *C12N 2501/15* (2013.01); *C12N 2501/155* (2013.01); *C12N 2501/415* (2013.01); *C12N 2506/45* (2013.01)

(58) Field of Classification Search
CPC .............. C12N 5/0618; C12N 2501/15; C12N 2501/155; C12N 2501/415; C12N 2506/45; G01N 33/5082
See application file for complete search history.

(56) References Cited

U.S. PATENT DOCUMENTS

| | | | |
|---|---|---|---|
| 2008/0044901 A1 | 2/2008 | Sasai et al. |
| 2016/0289635 A1 | 10/2016 | Sasai et al. |
| 2017/0313976 A1 | 11/2017 | Kuwahara et al. |
| 2019/0100724 A1 | 4/2019 | Sato et al. |

FOREIGN PATENT DOCUMENTS

| | | | |
|---|---|---|---|
| CN | 107109367 A | 8/2017 |
| CN | 109072179 A | 12/2018 |
| CN | 106103702 A | 11/2019 |
| WO | WO 2005/123902 A1 | 12/2005 |
| WO | WO 2015/076388 A1 | 5/2015 |
| WO | WO 2016/063985 A1 | 4/2016 |

OTHER PUBLICATIONS

Bamba, Yohei, et al. Journal of Neuroscience Methods 289 (2017): 57-63 (Year: 2017).*
Iovino, Mariangela, et al. Brain 138.11 (2015): 3345-3359 (Year: 2015).*
Clevers, Hans. Cell 165.7 (2016): 1586-1597 (Year: 2016).*
Nonaka T, et al. J Biol Chem. Nov. 5, 2010;285(45):34885-98 (Year: 2010).*
Qian, Xuyu, et al. Cell 165.5 (2016): 1238-1254 (Year: 2016).*
Lancaster, Madeline A., et al. Nature biotechnology 35.7 (2017): 659-666 (Year: 2017).*
Shi, Yichen, et. al. Nature protocols 7.10 (2012): 1836-1846 (Year: 2012).*
Extended European Search Report issued Dec. 12, 2023, in corresponding European Patent Application No. 20886120.3, 15 pages.
Jinsoo Seo et al: "Inhibition of p25/Cdk5 Attenuates Tauopathy in Mouse and iPSC Models of Frontotemporal Dementia" The Journal of Neuroscience, vol. 37, No. 41, 2017, pp. 9917-9924, XP093102574, US ISSN: 0270-6474, DOI: 10.1523/JNEUROSCI.0621-17.2017.
X. Medda et al: "Development of a Scalable, High-Throughput-Compatible Assay to Detect Tau Aggregates Using iPSC-Derived Cortical Neurons Maintained in a Three-Dimensional Culture Format", Slas Discovery: Advancing Life Sciences R&D, vol. 21, No. 8, Sep. 1, 2016, pp. 804-815, XP093102578, ISSN: 2472-5552, DOI: 10.1177/1087057116638029.
An Verheyen et al: "Genetically Engineered iPSC-Derived FTDP-17 MAPT Neurons Display Mutation-Specific Neurodegenerative and Neurodevelopmental Phenotypes", Stem Cell Reports, vol. 11, No. 2, Aug. 2018, pp. 363-379, XP93102567, United States ISSN: 2213-6711, DOI: 10.1016/j.stemcr.2018.06.022 Verheyen: "Genetically Engineered iPSC-Derived FTDP-17 MAPT Neurons Display Mutation-Specific Neurodegenerative and Neurodevelopmental Phenotypes Document S1" (Supplemental Information), Aug. 14, 2018, XP093104222, Retrieved from the Internet: URL:https://www.ncbi.nlm.nih.gov/pmc/articles/PMC6093179/bin/mmc1.pdf [retrieved on Nov. 21, 2023].

(Continued)

*Primary Examiner* — Peter Paras, Jr.
*Assistant Examiner* — Zanna Maria Beharry
(74) *Attorney, Agent, or Firm* — Oblon, McClelland, Maier & Neustadt, L.L.P.

(57) ABSTRACT

According to a production method for a brain organoid, comprising a step 1 of carrying out suspension culture of human pluripotent stem cells having a mutation in at least one or more base sequences in an exon selected from the group consisting of an exon 9, an exon 10, an exon 11, an exon 12, and an exon 13 of a microtubule-associated protein tau (MAPT) gene, and having a mutation in at least one or more base sequences in an intron 10 of the MAPT gene, it is possible to produce a brain organoid having a phosphorylated 3-repeat tau protein and a phosphorylated 4-repeat tau protein.

6 Claims, 8 Drawing Sheets

Specification includes a Sequence Listing.

(56) References Cited

OTHER PUBLICATIONS

Karl Grenier et al: "Three-dimensional modeling of human neurodegeneration: brain organoids coming of age", Molecular Psychiatry, Nature Publishing Group UK, London, vol. 25, No. 2, Aug. 23, 2019, pp. 254-274, XP036993096, ISSN: 1359-4184, DOI: 10.1038/S41380-019-0500-7 [retrieved on Aug. 23, 2019].

Combined Chinese Office Action and Search Report issued Jun. 3, 2023, in corresponding Chinese Patent Application No. 202080074604.4 (with English Translation), 17 pages.

Madeline A Lancaster, et. al., "Generation of cerebral organoids from human pluripotent stem cells", Nature protocols, vol. 9, No. 10, Sep. 4, 2014, pp. 2329-2340.

Verheyen, A. et al., "Genetically Engineered iPSC-Derived FTDP-17 MAPT Neurons Display Mutation-Specific Neurodegenerative and Neurodevelopmental Phenotypes", Stem Cell Reports, Aug. 14, 2018, vol. 11, pp. 363-379.

Garcia-Leon, J.A. et al., "Generation of a human induced pluripotent stem cell-based model for tauopathies combining three microtubule-associated protein TAU mutations which displays several phenotypes linked to neurodegeneration", Alzheimer's & Dementia 14, 2018, pp. 1261-1280.

Nakamura, M. et al., "Pathological Progression Induced by the Frontotemporal Dementia-Associated R406W Tau Mutation in Patient-Derived iPSCs", Stem Cell Reports, 2019, vol. 13, pp. 684-699.

Sahara, N., "Development of imaging-based diagnostic procedures for brain protein aging using a mouse model of tauopathy", Folia Pharmacologica Japonica, 2018, vol. 152, pp. 4-9.

International Search Report mailed on Jan. 12, 2021 in PCT/JP2020/041351 filed on Nov. 5, 2020, 7 pages).

* cited by examiner

BRAIN ORGANOID AND USE THEREOF

TECHNICAL FIELD

The present invention relates to a brain organoid and use thereof. More specifically, the present invention relates to a production method for a brain organoid, a brain organoid, and a drug efficacy evaluation method. Priority is claimed on Japanese Patent Application No. 2019-201231, filed on Nov. 6, 2019, the content of which is incorporated herein by reference.

BACKGROUND ART

A tau protein is a product from a microtubule-associated protein tau (abbreviated as "MAPT") gene located on chromosome 17 in humans, and it contributes to the construction and maintenance of neural axons. The tau protein is roughly classified into a 3-repeat tau protein having three repeating sequences involved in microtubule binding and a 4-repeat tau protein having four repeating sequences. In a case where any of them is excessively phosphorylated, it loses the ability to bind to microtubules and self-aggregate. Then, in a case where a large amount of self-aggregate accumulates in the brain, it is conceived that dementia is caused.

A method of two-dimensionally culturing an induced pluripotent stem cell is known in which three mutations of N279K, P301L, and E10+16 are introduced into the MAPT gene thereby producing a cultured nerve cell having a phosphorylated 3-repeat tau protein as a cultured nerve cell having tau protein (see Non-Patent Document 1).

In addition, a method of two-dimensionally culturing an induced pluripotent stem cell is known in which two mutations of P301S, and E10+16 are introduced into the MAPT gene thereby producing a cultured nerve cell having a phosphorylated 3-repeat tau protein (see Non-Patent Document 2).

CITATION LIST

Non-Patent Documents

[Non-Patent Document 1]

Verheyen A., et al., Genetically Engineered iPSC-Derived FTDP-17 MAPT Neurons Display Mutation-Specific Neurodegenerative and Neurodevelopmental Phenotypes, Stem Cell Reports, 11 (2), 363-379, 2018.

[Non-Patent Document 2]

Garcia-Leon J. A., et al., Generation of a human induced pluripotent stem cell-based model for tauopathies combining three microtubule-associated protein TAU mutations which displays several phenotypes linked to neurodegeneration, Alzheimers Dement., 14 (10), 1261-1280, 2018.

SUMMARY OF INVENTION

Technical Problem

In Alzheimer's disease and senile dementia of the neurofibrillary tangle type, which is one kind of frontotemporal lobar degeneration (hereinafter, also referred to as "FTLD-tau") associated with accumulation of tau protein, it is known that both 3-repeat tau protein and 4-repeat tau protein accumulate. For this reason, in the pathological elucidation and drug efficacy evaluation of FTLD-tau using cultured nerve cells, a brain organoid in which both phosphorylated 3-repeat tau protein and phosphorylated 4-repeat tau protein have accumulated is required.

An object of the present invention is to provide a brain organoid in which a phosphorylated 3-repeat tau protein and a phosphorylated 4-repeat tau protein have accumulated and a production method thereof, as well as a drug efficacy evaluation method using the brain organoid.

Solution to Problem

The present invention includes the following embodiments.

[1] A production method for a brain organoid, including a step 1 of carrying out suspension culture of human pluripotent stem cells having a mutation in at least one or more base sequences in an exon selected from the group consisting of an exon 9, an exon 10, an exon 11, an exon 12, and an exon 13 of a microtubule-associated protein tau (MAPT) gene, and having a mutation in at least one or more base sequences in an intron 10 of the MAPT gene.

[2] The production method for a brain organoid according to [1], in which the base sequence mutation in the exon is mutations in two or more base sequences.

[3] The production method for a brain organoid according to [2], in which the base sequence mutation in the exon includes mutations in base sequences in the exon 10, encoding amino acid mutations of N279K and P301S.

[4] The production method for a brain organoid according to any one of [1] to [3], in which the base sequence mutation in the intron 10 includes a base sequence mutation of E10+16.

[5] The production method for a brain organoid according to any one of [1] to [4], in which the base sequence mutation in the exon is mutations in base sequences in the exon 10, encoding amino acid mutations of N279K and P301S, and the base sequence mutation in the intron 10 is a base sequence mutation of E10+16.

[6] The production method for a brain organoid according to any one of [1] to [5], in which the suspension culture in the step 1 is carried out in a culture medium 1 containing an inhibitor of a bone morphogenetic protein (BMP) signal transduction pathway and an inhibitor of a transforming factor β (transforming growth factor β, TGF-β) family signal transduction pathway.

[7] The production method for a brain organoid according to any one of [1] to [6], further including a step 2 of culturing a culture preparation formed by the suspension culture of the step 1 in a culture medium 2 containing an enhancing agent of Wnt signaling and an extracellular matrix; and a step 3 of culturing a culture preparation formed by the culture of the step 2 in a culture medium 3 containing no extracellular matrix.

[8] A production method for a brain organoid, further including a step 4 of dispersing the brain organoid produced by the production method for a brain organoid according to any one of [1] to [7] to obtain a dispersion; and a step 5 of culturing the dispersion in the presence of a tau protein aggregate.

[9] The production method for a brain organoid according to [8], in which the culturing in the step 5 is carried out in the presence of 0.0005 ng to 0.4 ng of the tau protein aggregate per one cell contained in the dispersion.

[10] The production method for a brain organoid according to [8] or [9], in which the tau protein aggregate includes an aggregate of a recombinant tau protein.

[11] The production method for a brain organoid according to [10], in which the recombinant tau protein is encoded by a MAPT gene having a base sequence mutation in an exon 10.

[12] The production method for a brain organoid according to any one of [8] to [11], in which the culturing in the step 5 is carried out in the presence of a phosphorylation-accelerating reagent.

[13] A brain organoid having a misfolded 3-repeat tau protein and a misfolded 4-repeat tau protein.

[14] The brain organoid according to [13], in which the misfolded 3-repeat tau protein includes a phosphorylated 3-repeat tau protein and the misfolded 4-repeat tau protein includes a phosphorylated 4-repeat tau protein.

[15] The brain organoid according to [14], in which a detection signal of the phosphorylated 4-repeat tau protein shown by a Western blot method is 0.5 or more with respect to a detection signal of 1 of the phosphorylated 3-repeat tau protein.

[16] The brain organoid according to [14] or [15], in which the phosphorylated 4-repeat tau protein is a phosphorylated 0N4R tau protein.

[17] The brain organoid according to [14] or [16], in which the phosphorylated 3-repeat tau protein is a phosphorylated 0N3R tau protein.

[18] A drug efficacy evaluation method including a step of bringing the brain organoid according to any one of [13] to [17] into contact with a test substance; and a step of examining an effect of the test substance on the brain organoid.

[19] The drug efficacy evaluation method according to [18], further including a step of transplanting the brain organoid according to any one of [13] to [17] into a brain of a mammal before the step of bringing the brain organoid into contact with a test substance.

It can also be said that the present invention includes the following embodiments.

[P1] A production method for a brain organoid, including a step of carrying out suspension culture on mutant-induced pluripotent stem cells or a cell aggregate thereof, which have a mutation in at least one or more base sequences in an exon 9 to an exon 13 of a microtubule-associated protein tau gene and having a mutation in at least one or more base sequences in an intron 10 of a microtubule-associated protein tau gene.

[P2] The production method for a brain organoid according to [P1], in which the base sequence mutation in the exon 9 to the exon 13 is mutations in two or more base sequences.

[P3] The production method for a brain organoid according to [2], in which the base sequence mutation in the exon 9 to the exon 13 includes mutations in bases in the exon 10, encoding amino acid mutations of N279K and P301S.

[P4] The production method for a brain organoid according to any one of [P1] to [P3], in which the base sequence mutation in the intron 10 is a mutation in one or more base sequences.

[P5] The production method for a brain organoid according to [P4], in which the base sequence mutation in the intron 10 is a mutation including E10+16.

[P6] The production method for a brain organoid according to any one of [P1] to [P5], in which the step of carrying out suspension culture on the mutant-induced pluripotent stem cells or a cell aggregate thereof includes a step of carrying out suspension culture on the mutant-induced pluripotent stem cells or a cell aggregate thereof in a culture medium containing an inhibitor of a bone morphogenetic protein (BMP) signal transduction pathway and an inhibitor of a transforming factor β (transforming growth factor β, TGF-β) family signal transduction pathway; a step of carrying out suspension culture in a culture medium containing an extracellular matrix; and a step of carrying out suspension culture in a culture medium containing no extracellular matrix.

[P7] The production method for a brain organoid according to [P6], in which the culture medium containing the extracellular matrix is a culture medium mixed with the extracellular matrix.

[P8] The production method for a brain organoid according to [P7], in which the culture medium containing the extracellular matrix is a culture medium containing an inhibitor of a TGF-β family signal transduction pathway and a Wnt signal-enhancing agent.

[P9] The brain organoid, in which the brain organoid is produced by the production method for a brain organoid according to any one of [P1] to [P8].

[P10] A brain organoid having a phosphorylated 3-repeat tau protein and a phosphorylated 4-repeat tau protein.

[P11] The brain organoid according to [P10], in which a detection signal of the phosphorylated 4-repeat tau protein shown by a Western blot method is 0.5 or more with respect to a detection signal of 1 of the phosphorylated 3-repeat tau protein.

[P12] The brain organoid according to [P10] or [P11], in which the phosphorylated 4-repeat tau protein is a phosphorylated 0N4R tau protein.

[P13] The brain organoid according to [P10] or [P12], in which the phosphorylated 3-repeat tau protein is a phosphorylated 0N3R tau protein.

[P14] A drug efficacy evaluation method including a step of bringing the brain organoid according to any one of [P9] to [P13] into contact with a test substance; and a step of examining an effect of the test substance on the brain organoid.

[P15] The drug efficacy evaluation method according to [P14], further including a step of transplanting the brain organoid according to any one of [P9] to [P13] into a brain of a mammal before the step of bringing the brain organoid into contact with a test substance.

[P16] A kit for producing a brain organoid, including a mutant-induced pluripotent stem cell which has a mutation in at least one or more base sequences in an exon 9 to an exon 13 of a microtubule-associated protein tau gene and in at least one or more base sequences in an intron 10; a culture medium containing an inhibitor of a BMP signal transduction pathway and an inhibitor of a TGF-β family signal transduction pathway; a culture medium containing an extracellular matrix; and a culture medium containing no extracellular matrix.

Advantageous Effects of Invention

According to the production method for a brain organoid according to one embodiment of the present invention, it is possible to produce a brain organoid in which a phosphorylated 3-repeat tau protein and a phosphorylated 4-repeat tau protein have accumulated.

DESCRIPTION OF EMBODIMENTS

Figure 1:
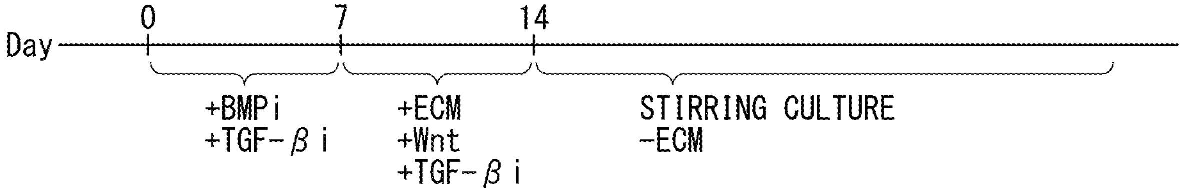
FIG. 1 is a schematic diagram showing a preparation schedule of a human brain organoid.

Hereinafter, the present invention will be described in more detail with reference to embodiments, but the present invention is not limited to the following embodiments.

Unless otherwise specified, each component exemplified in the present specification, for example, one kind of component that is contained in a culture medium or one kind of component that is used in each step can be used, or two or more kinds thereof can be used in combination.

In the present specification, the notation indicating a numerical range such as "A to B" is synonymous with "A or more and B or less", and A and B shall be included in the numerical range.

[Production Method for Brain Organoid]

A production method for a brain organoid of the present embodiment has a step 1 of carrying out suspension culture of human pluripotent stem cells (mutant human pluripotent stem cells, hereinafter also referred to as "mhPSCs") having a gene mutation in at least one or more base sequences in an exon selected from the group consisting of an exon 9, an exon 10, an exon 11, an exon 12, and an exon 13 (hereinafter, may be referred to as "an exon 9 to an exon 13") of a human microtubule-associated protein tau gene (a MAPT gene), and having a mutation in at least one or more base sequences in an intron 10 of the MAPT gene.

A cell aggregate is formed by the suspension culture of the step 1. The cell aggregate means a mass formed by the adhesion of two or more cells. In a case where cell aggregates are induced to differentiate, a brain organoid can be produced. Examples of the method of inducing differentiation of cell aggregates include a method including a step 2 of carrying out culture in a culture medium 2 containing an enhancing agent of Wnt signaling and an extracellular matrix (hereinafter, also referred to as "ECM"), and a step 3 of culturing a culture preparation formed by the culture of the step 2 in a culture medium 3 containing no extracellular matrix.

The suspension culture refers to carrying out culture while maintaining a state in which culture cells are suspended in a culture solution under the conditions in which the culture cells are allowed to adhere to the culture surface of a culture container (hereinafter, also referred to as "culture vessel") and a method of carrying out the culture. In the suspension culture, it is preferable to carry out three-dimensional culture.

The culture vessel that is used in the suspension culture is preferably a culture vessel of which the culture surface is cell non-adhesive. Examples of the culture vessel of which the culture surface is cell non-adhesive include culture vessels such as a 24-well plate, a 48-well plate, a 96-well plate, and a stack plate, where the surface of the culture surface thereof has been subjected to a cell non-adhesive treatment with a 2-methacryloyloxyethyl phosphorylcholine polymer or the like or has been processed to have an uneven shape. The culture vessel that is used in the suspension culture is preferably a V-bottom or U-bottom culture vessel so that the cultured cells can aggregate with each other.

The mhPSCs are obtained by genetically modifying at least one or more base sequences (one or more bases) in the exon 9 to the exon 13 of the MAPT gene in the genome of the wild-type human pluripotent stem cells (hereinafter, also referred to as "hPSCs"), and at least one or more base sequences (one or more bases) in the intron 10. Hereinafter, the genetically modified MAPT gene is also referred to as "the modified MAPT gene". The mhPSCs can be subjected to expansion culture.

Examples of the hPSCs include human embryonic stem cells (hESCs) and induced pluripotent stem cells (hiPSCs). Among these, hiPSCs are preferable.

The modified MAPT gene can be introduced into the genome of hSPCs by a genome editing technique using, for example, a transcription activating factor-like effector nuclease, a Zn finger nuclease, or CRISPR-Cas9. Among the above, CRISPR-Cas9 is preferable since a target gene can be inserted into a site of interest with high selectivity.

A CRISPR-Cas9 system is a system employed by bacteria and archaebacteria, where the CRISPR-Cas9 system utilizes a locus that functions as one kind of acquired immunity against nucleic acids such as viral DNA, viral RNA, and plasmid DNA, which have invaded from the outside. In order to introduce the modified MAPT gene into a host DNA by the CRISPR-Cas9 system, a vector for cleaving an introduction site of the host DNA is prepared. For this purpose, an expression vector encoding a guide RNA that guides Cas9 to a site of interest and a Cas9 protein expression vector are required. In a case where these two kinds of expression vectors and a donor DNA containing the modified MAPT gene are introduced, the site of interest is cleaved, and then the modified MAPT gene is introduced by homologous recombination repair with the donor DNA. As the expression vector, it is possible to use one vector (one all-in-one vector) expressing both the guide RNA and the Cas9 protein instead of the two kinds of expression vectors.

It suffices that the sequence (the donor DNA) homologous to a site on the genome, the site being subjected to insertion, be operably linked upstream (the 5' side) or downstream (the 3' side) of the modified MAPT gene, and the length thereof is usually, 0.5 kb to 8 kb.

Examples of the method of introducing an expression vector or a donor DNA into hPSCs include a calcium phosphate method, an electroporation method, a lipofection method, an aggregation method, a microinjection method, a particle gun method, and a DEAE-dextran method.

Examples of the expression vectors include Escherichia coli-derived plasmids such as pBR322, pBR325, pUC12, pUC13, and pUC57; *Bacillus subtilis*-derived plasmids such as pUB110, pTP5, and pC194; yeast-derived plasmids such as pSH19 and pSH15; bacteriophages such as λ phage; viruses such as adenovirus, adeno-associated virus, lentivirus, vaccinia virus, and baculovirus; and vectors obtained by modifying these.

The modified MAPT gene can be introduced together with a tag sequence, a promoter sequence, a transcription termination sequence, a drug selection marker gene, and a combination thereof. Examples of the tag sequence include a fluorescent tag, an affinity tag, a degron tag, a localization tag. In particular, in a case where the modified MAPT gene is allowed to have a drug selection marker, it is possible to efficiently select cells in which the modified MAPT gene has been introduced, by drug selection.

Examples of the drug selection marker gene include a neomycin resistance gene, a histidinol resistance gene, a puromycin resistance gene, a hygromycin resistance gene, a blasticidin resistance gene, an ampicillin resistance gene, and a chloramphenicol resistance gene. In a case where a drug selection marker gene is introduced into the tag sequence, the drug selection marker gene-introduced tag sequence can be removed after drug selection.

The MAPT gene (NCBI accession number: NG_007398.1) is present on human chromosome 17 long arm 17q21 and has 16 exons and 15 introns. The modified MAPT gene is a modified MAPT gene obtained by modifying at least one or more bases in the exon 9 to the exon 13 of the MAPT gene and at least one or more bases in the intron 10.

A plurality of base sequence mutations of the MAPT gene are known to cause frontotemporal lobar degeneration associated with the accumulation of tau protein. Further, it is known that the mutation sites of base sequences of the MAPT gene are concentrated in the ranges of the base sequences in the exon 9 to the exon 13 and the base sequences in the intron 10.

As the modified MAPT gene, it is possible to use a modified MAPT gene obtained by modifying at least one or more base sequences in the exon 9 to the exon 13 of the MAPT gene and at least one or more in the intron 10. Among these, the number of base sequence mutations in the exon 9 to the exon 13 is preferably two or more and more preferably two. Further, the number of base sequence mutations in the intron 10 is preferably one or more and more preferably one.

Examples of the base sequence mutation of the modified MAPT gene include a base sequence mutation in the exon 9, such as a base sequence mutation encoding an amino acid mutation of K257V, K257T, I260V, L266V, or G272V; a base sequence mutation in the exon 10, such a base sequence mutation encoding an amino acid mutation of N279K, ΔK280, L284L, N296N, N296H, ΔN296, P301L, P301S, P301T, G303V, S305N, or S305S; a base sequence mutation in the exon 11, such as a base sequence mutation encoding an amino acid mutation of L315L, L315R, S320Y, S310F; a base sequence mutation in the exon 12, such as a base sequence mutation encoding an amino acid mutation of V337M, E342V, G335V, G335S, Q336R, or K369I; and a base sequence mutation in the exon 13, such as a base sequence mutation encoding an amino acid mutation of G389R or R406W. Further, examples of the base sequence mutation in the intron 10 include E10+3, E10+11, E10+12, E10+13, E10+14, E10+16, and E10+19.

The base sequence mutation in the exon 9 to the exon 13 is preferably a base sequence mutation of the exon 10, and the base sequence mutation in the exon 10 is preferably N279K or P301S. The base sequence mutation in the intron 10 is preferably E10+16. In a case where a modified MAPT gene obtained by these modifications is used, it is possible to efficiently produce a brain organoid having a phosphorylated 3-repeat tau protein and a phosphorylated 4-repeat tau protein.

The hiPSCs means cells in which pluripotency has been induced by reprogramming human somatic cells by a known method or the like.

Examples of the combination of reprogramming factors include a combination of Oct3/4, Sox2, Klf4, and Myc (c-Myc or L-Myc); and a combination of Oct3/4, Sox2, Klf4, Lin28, and L-Myc.

As the hiPSCs, hiPSCs established as cell lines can be used. The hiPSCs established as cell lines, such as a 201B7 cell, a 201B7-Ff cell, a 253G1 cell, a 253G4 cell, a 1201C1 cell, a 1205D1 cell, a 1210B2 cell, and a 1231A3 cells, are available from Kyoto University or iPS Academia Japan, Inc. In addition, the hiPSCs established as cell lines, such as PCPhiPS771, are available from REPROCELL Inc. Further, the hiPSCs established as cell lines, such as XFiPS-F44-3F-2, are available from the Institute of Health Carlos III.

The expansion culture is an operation of proliferating mhPSCs. In the expansion culture, it is preferable to carry out two-dimensional culture by adhesion culture. The adhesion culture is a culture carried out by allowing the adhesion between cell aggregates and the culture surface of a culture vessel. The expansion culture is usually carried out in an environment of 30° C. to 50° C. and a carbon dioxide content rate of 1% by volume to 15% by volume.

As the culture vessel that is used in the adhesion culture, it is possible to use the same culture vessels as those described above, provided that the culture surface of the culture vessel is cell adhesive. Examples of the surface treatment for improving adhesiveness include coating of laminin such as laminin α5β1γ1, laminin α1β1γ1, laminin 511E8, entactin, collagen, gelatin, vitronectin, polylysine, or polyornithine, and positive charge treatment.

The culture medium that is used in the expansion culture (hereinafter, also referred to as an "expansion culture medium") is preferably a feeder-free culture medium. Examples of the feeder-free culture medium include known culture media such as an hES9 culture medium, an hES9a culture medium, and an hESF-FX culture medium, and commercially available products such as TESR™-E8™ (a feeder-free, animal component-free culture medium for human embryonic stem(ES) cells and human induced pluripotent stem (iPS) cells) (product name, manufactured by STEMCELL Technologies) and STEMFIT® (animal-origin free, chemically defined media that maintain induced pluripotent stem cells (iPSCs) and embryonic stem cells (ESCs) under feeder-free conditions during the reprogramming, expansion and differentiation phases of stem cell culture and growth medium) (registered trade name).

In order to suppress cell death, the culture can be carried out in, as the expansion culture medium, a culture medium containing a ROCK inhibitor in the feeder-free culture medium before carrying out culture in the feeder-free culture medium. In a case where a culture medium obtained by adding a ROCK inhibitor to a feeder-free culture medium is used, the culture period may be at most 5 days, and then the culture is carried out in a feeder-free culture medium containing no ROCK inhibitor, usually for 1 day or more and preferably for 3 days or more.

Examples of the ROCK inhibitor include Y-27632 (CAS number: 129830-38-2), Fasudil/HA1077 (CAS number:

105628-07-7), H-1152 (CAS number: 871543-07-6), and Wf-536 (CAS No.: 539857-64-2), as well as derivatives thereof.

The concentration of the ROCK inhibitor contained in the expansion culture medium is such that the concentration is usually 0.1 μM to 100 μM, the concentration is preferably 1 μM to 80 μM, and the concentration is more preferably 5 μM to 50 μM.

Before carrying out expansion culture, the mhPSCs can be dispersed. The dispersion means separating cells into a cell population of 100 or less, preferably a cell population of 50 or less, and more preferably single cells, by a dispersion treatment such as an enzyme treatment or a physical treatment. Examples of the dispersion treatment include a mechanical dispersion treatment, a cell dispersion liquid treatment, and a treatment of adding a cell-protecting agent. These treatments can be combined. Among these, a cell dispersion liquid treatment is preferable.

Examples of the cell dispersion liquid that is used in the cell dispersion liquid treatment include a solution containing any of enzymes such as trypsin, collagenase, hyaluronidase, elastase, pronase, DNase, and papain; and a chelating agent such as ethylenediaminetetraacetic acid. Examples of the commercially available cell dispersion liquid include TRYPLE™ Select and TRYPLE™ Express manufactured by Thermo Fisher Scientific, Inc., and Nerve Cell Dispersion Liquid A (catalog number: SBMBX0801D-2A) manufactured by KAC Co., Ltd. Examples of the mechanical dispersion treatment include a pipetting treatment and a scraping operation with a scraper.

Before the dispersion treatment, a treatment with a cell-protecting agent can be carried out to prevent cell death. Examples of the cell-protecting agent include fibroblast growth factor (hereinafter, also referred to as "FGF"), heparin, a ROCK inhibitor, an insulin-like growth factor (hereinafter, also referred to as "IGF"), serum, and a serum substitute.

In the step 1, the mhPSCs are subjected to suspension culture in the culture medium 1 to form a cell aggregate. Hereinafter, the cell aggregate formed by the suspension culture of the step 1 is also referred to as a cell aggregate 1. The culture vessel that is used in the step 1 is preferably a culture vessel of which the culture surface is cell non-adhesive, which similar to that described above.

The culture medium 1 preferably contains an inhibitor of a BMP signal transduction pathway associated with the phosphorylation of Smad1/5/9 and an inhibitor of an inhibitor of a TGF-β signal transduction pathway associated with the phosphorylation of Smad2/3. The culture medium 1 is generally prepared by adding an inhibitor of a BMP signal transduction pathway, an inhibitor of a TGF-β signal transduction pathway, and the like to a basal culture medium.

Examples of the basal culture medium include a BME culture medium, a BGJb culture medium, a CMRL 1066 culture medium, a Glasgow's MEM (GMEM) culture medium, an Improved MEM Zinc Option culture medium, an IMDM culture medium, a Medium 199 culture medium, an Eagle's MEM culture medium, an αMEM culture medium, a DMEM culture medium, a F-12 culture medium, a DMEM/F12 culture medium, an IMDM/F12 culture medium, a Ham's culture medium, an RPMI 1640 culture medium, and a Fisher's culture medium; and a mixed culture medium thereof.

Examples of the inhibitor of the BMP signal transduction pathway include chordin, nogin, follistatin, and dorsomorphin (6-[4-(2-pyrimidine-1-yl-ethoxy)phenyl]-3-pyridine-4-yl-pyrazolo[1,5-a]pyrimidine), DMH1 (4-[6-(4-isopropoxyphenyl)pyrazolo[1,5-a]pyrimidine-3-yl]quinoline, 4-[6-[4-1-methylethoxy)phenyl]pyrazolo[1,5-a]pyrimidine-3-yl]-quinoline), and LDN193189 (4-(6-(4-(piperidine-1-yl) phenyl)pyrazolo[1,5-a]]pyrimidine-3-yl)quinoline). Among these, dorsomorphin or LDN193189 is preferable.

The concentration of the inhibitor of the BMP signal transduction pathway contained in the culture medium 1 is usually 0.5 μM to 10 μM, preferably 0.75 μM to 5 μM, and more preferably 1 μM to 3 μM.

The inhibitor of the TGF-β signal transduction pathway is a substance that inhibits a signal transduction pathway transduced by the phosphorylation of Smad2/3, and it is preferably a substance that selectively inhibits the kinase activity of the TGF-βI type receptor kinase (ALK5). Examples of the inhibitor of the TGF-β signal transduction pathway include A83-01 (CAS number: 909910-43-6), SB-431542 (CAS number: 301836-41-9), SB-505124 (CAS number: 694433-59-5), SB-525334 (CAS number: 356559-20-1), LY364947 (CAS number: 396129-53-6), SC-203294 (CAS number: 627536-09-08), SD-208 (CAS number: 627536-09-8), and SJN2511 (CAS number: 446859-33-2). Among these, A83-01 or SB-431542 is preferable.

The concentration of the inhibitor of the TGF-β signal transduction pathway contained in the culture medium 1 is usually 0.5 μM to 10 μM, preferably 0.75 μM to 5 μM, and more preferably 1 μM to 3 μM.

The culture medium 1 can further contain a neurobiological supplement, a culture medium supplement, serum, a serum substitute, and an antibacterial agent, as well as a serum-derived protein such as insulin or albumin.

Examples of the neurobiological supplement include a B-27™ supplement (serum-free supplement for support the low-or high-density growth and short-or long-term viability of embryonic. post-natal, and adult hippocampal and other CNS neurons) (product name, manufactured by Thermo Fisher Scientific, Inc.) containing biotin, cholesterol, linoleic acid, linolenic acid, progesterone, putrescine, retinol, retinyl acetate, sodium selenite, triiodothyronine (T3), DL-α-tocopherol (vitamin E), albumin, insulin, and transferrin; and a N2 supplement containing human transferrin, bovine insulin, progesterone, putrescine, and sodium selenite.

Examples of the culture medium supplement include a glutamic acid-containing supplement such as "GLUTAMAX™ supplement" (a dipeptide, L-alanyl-L-glutamine) (product name, manufactured by Thermo Fisher Scientific, Inc.) containing L-glutamic acid and a dipeptide obtained from L-glutamic acid, an amino acid solution such as "MEM Non-Essential Amino Acids Solution" (product name, manufactured by Thermo Fisher Scientific, Inc.), and 2-mercaptoethanol.

Examples of the antibacterial agent include a penicillin-based antibiotic, a cephem-based antibiotic, a macrolide antibiotic, a tetracycline-based antibiotic, a fosfomycin-based antibiotic, an aminoglycoside-based antibiotic, and a new quinolone antibiotic.

The culture period of the step 1 is usually 1 day or more, preferably 3 to 14 days, and more preferably 4 to 12 days.

The culture of the step 1 is carried out in an environment in which the temperature is usually 30° C. to 50° C., preferably 32° C. to 48° C., and more preferably 34° C. to 46° C., and the carbon dioxide content rate is usually 1% by volume to 15% by volume, preferably 2% by volume to 14% by volume, and more preferably 3% by volume to 13% by volume. In addition, it is also possible to carry out culture in an atmosphere of a high oxygen concentration.

Before carrying out the suspension culture in the culture medium 1, it is possible to disperse the cell aggregates of mhPSCs, which are formed by expansion culture. The treatment method for dispersion is the same as the treatment method for dispersion described in the expansion culture.

In the production method for a brain organoid of the present embodiment, the culture preparation (the cell aggregate 1) formed in the suspension culture of the step 1 is induced to differentiate, whereby it is possible to produce a brain organoid in which a phosphorylated 3-repeat tau protein and a phosphorylated 4-repeat tau protein have accumulated. Examples of the method of inducing differentiation include a method including the step 2 of culturing the cell aggregate 1 in the culture medium 2 containing an enhancing agent of Wnt signaling and ECM, and the step 3 of culturing a culture preparation formed by the culture of the step 2 in the culture medium 3 containing no extracellular matrix.

The step 2 may be continuously carried out by replacing the culture medium 1 with the culture medium 2 without taking out the cell aggregate 1 from the culture medium 1 or can be carried out by taking out the cell aggregate 1 from the culture medium 1 and seeding it in the culture medium 2. The culture of the step 2 is preferably a suspension culture.

The culture period of the culture of the step 2 is usually 1 day or more, preferably 3 to 14 days, and more preferably 4 to 12 days.

The culture of the step 2 is carried out in an environment in which the temperature is usually 30° C. to 50° C., preferably 32° C. to 48° C., and more preferably 34° C. to 46° C., and the carbon dioxide content rate is usually 1% by volume to 15% by volume, preferably 2% by volume to 14% by volume, and more preferably 3% by volume to 13% by volume. In addition, it is also possible to carry out culture in an atmosphere of a high oxygen concentration.

The culture vessel that is used in the culture of the step 2 is preferably a culture vessel of which the culture surface is a cell non-adhesive culture vessel, which is the same as that in the step 1. The details of the cell non-adhesive culture vessel are the same as those in the step 1.

The culture medium 2 is a culture medium containing ECM. Examples of the method of carrying out culture in a culture medium containing ECM include a method of embedding the cell aggregate 1 in ECM and carrying out culture thereof and a method of culturing the cell aggregate 1 in a culture medium mixed with ECM. Among these, a method of culturing the cell aggregate 1 in a culture medium mixed with ECM is preferable.

The culture medium mixed with ECM is prepared by carrying out mixing so that the volume of ECM is usually 1% by volume or more, preferably 5% by volume to 100% by volume, and more preferably 10% by volume to 90% with respect to the volume of components other than the ECM in the culture medium, and then gelating an ECM precursor. Examples of the method of mixing the ECM precursor and the components other than ECM include a method of carrying out pipetting on an ice bath. The culture medium mixed with ECM means a medium having the ECM that is not visually observed in the culture medium.

The culture medium 2 is usually prepared by adding ECM or an ECM precursor to a basal culture medium. Examples of the basal culture medium include a BME culture medium, a BGJb culture medium, a CMRL1066 culture medium, GMEM (product name, manufactured by Thermo Fisher Scientific, Inc.), an Improved MEM Zinc Option culture medium (product name, manufactured by Thermo Fisher Scientific, Inc.), an IMDM culture medium, Medium 199 (product name, manufactured by Thermo Fisher Scientific, Inc.), an Eagle's MEM culture medium, an αMEM culture medium, a DMEM culture medium, a Ham's culture medium, a Ham's F-12 culture medium, and a RPMI1640 culture medium, as well as a mixture thereof.

Examples of the ECM include a component contained in the basement membrane and a glycoprotein present in the intercellular space. Examples of the component contained in the basement membrane include type IV collagen, laminin, heparan sulfate proteoglycan, and entactin. As the ECM, a commercially available product containing ECM can be used. Examples of the glycoprotein present in the intercellular space include collagen, laminin, entactin, fibronectin, and heparin sulfate. Examples of the commercially available product containing ECM include Matrigel (product name, manufactured by Corning Incorporated) and human type laminin (product name, manufactured by Sigma-Aldrich Co., LLC).

MATRIGEL® contains a basement membrane component derived from Engelbreth Holm Swarm mouse sarcoma. The main components of the MATRIGEL® are type IV collagen, laminin, heparan sulfate proteoglycan, and entactin; however, in addition to these, they include various growth factors such as epidermal growth factor (hereinafter, also referred to as "EGF"), nerve growth factor (hereinafter, also referred to as "NGF"), platelet-derived growth factor (hereinafter, also referred to as "PDGF"), and insulin-like growth factor I ((hereinafter, also referred to as "IGF-1"), as well as TGF-β. There is MATRIGEL® that is low in grade in terms of the concentrations of these components, and in such MATRIGEL®, the concentration of EGF is less than 0.5 ng/mL, the concentration of NGF is less than 0.2 ng/mL, the concentration of PDGF is less than 5 pg/mL, the concentration of IGF-1 is less than 5 ng/mL, and the concentration of TGF-β is less than 1.7 ng/mL. As MATRIGEL®, it is preferable to use MATRIGEL® that is low in grade in terms of the content rate of these components.

The culture medium 2 contains a Wnt signal-enhancing agent. Examples of the Wnt signal-enhancing agent include a GSK-3β inhibitor, a Wnt protein, and an LGR5 agonist. Among these, a GSK-3β inhibitor or a Wnt proteins is preferable. The final concentration of the Wnt signal-enhancing agent contained in the culture medium 2 is usually 0.1 μM to 10 μM, and preferably 0.2 μM to 5 μM.

Examples of the GSK-3β inhibitor include CHIR99021 (CAS number: 252917-06-9), kenpaullone (CAS number: 142273-20-9), and 6-bromoindirubin-3'-oxime (BIO, CAS number: 667463-62-9). Among these, CHIR99021 is preferable.

The Wnt protein is preferably a Wnt protein derived from mammals. Examples of the mammalian Wnt protein include Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16. Among these, Wnt3a is preferable. The Wnt protein is more preferably a complex with afamin.

Examples of the LGR5 agonist include the R-spongin family. Examples of the R-spongin family include R-spongin 1, R-spongin 2, R-spongin 3, and R-spongin 4, and among them, R-spongin 1 is preferable.

In a case where CHIR99021 is used as the Wnt signal-enhancing agent, the final concentration of CHIR99021 contained in the culture medium 2 is usually 0.1 μM to 30 μM and preferably 0.2 μM to 20 μM.

In a case where Wnt3a is used as the Wnt signal-enhancing agent, the final concentration of Wnt3a contained in the culture medium 2 is usually 0.1 ng/mL to 20 ng/mL and preferably 0.2 ng/mL to 10 ng/mL.

The culture medium 2 may contain an inhibitor of a TGF-β signal transduction pathway. Examples of the inhibitor of the TGF-β signal transduction pathway include the same ones as those in the culture medium 1 described above. Among these, SB-431542 or SC-203294, which can selectively inhibit the kinase activity of ALK5, is preferable. The final concentration of the inhibitor of the TGF-β signal transduction pathway contained in the culture medium 2 is usually 0.1 to 20 μM and preferably 0.1 μM to 10 μM.

The culture medium 2 can further contain a neurobiological supplement, a culture medium supplement, a serum-derived protein such as insulin or albumin, serum, and a serum substitute. The details of the neurobiological supplement and the culture medium supplement include the same ones as those described in the above-described culture medium 1.

The step 3 may be carried out continuously by replacing the culture medium 2 with the culture medium 3 without taking out the culture preparation of the step 2 from the culture medium 2 or can be carried out by taking out the culture preparation of the step 2 from the culture medium 2 and seeding the culture preparation in the culture medium 3. The culture of the step 3 is preferably a suspension culture, and the suspension culture is preferably carried out while stirring the culture medium.

The culture period of the step 3 is usually 1 day or more, preferably 2 days to 700 days, and more preferably 10 days to 365 days. The culture of the step 3 is carried out in an environment in which the temperature is usually 30° C. to 50° C., preferably 32° C. to 48° C., and more preferably 34° C. to 46° C., and the carbon dioxide content rate is usually 1% by volume to 15% by volume, preferably 2% by volume to 14% by volume, and more preferably 3% by volume to 13% by volume. In addition, it is also possible to carry out culture in an atmosphere of a high oxygen concentration.

The culture vessel that is used in the culture of the step 3 is preferably a cell non-adhesive culture vessel. The details of the cell non-adhesive culture vessel are the same as those in the step 1 described above.

The culture medium 3 does not contain ECM. "Does not contain ECM" means that ECM is not intentionally added to the culture medium 3, and thus ECM mixed as an unavoidable impurity at 5% by volume or less with respect to the volume of the components in the culture medium is allowed.

The culture medium 3 can further contain a neurobiological supplement, a culture medium supplement, a serum-derived protein such as insulin or albumin, serum, and a serum substitute. The details of the neurobiological supplement and the culture medium supplement include the same ones as those described in the above-described culture medium 1.

The culture medium 3 is generally prepared by adding other components such as a neurobiological supplement, a culture medium supplement, a serum-derived protein such as insulin or albumin, serum, and a serum substitute, to a basal culture medium. Examples of the basal culture medium include the same ones as the culture medium 1 described above.

The production method for a brain organoid of the present embodiment can further include a step 4 of dispersing the brain organoid formed by inducing the differentiation of the cell aggregate 1 formed in the suspension culture of the step 1, thereby obtaining a dispersion; and a step 5 of culturing the dispersion or cell aggregates formed by the aggregation of the dispersion, in the presence of the tau protein aggregates. By the steps 4 and 5, it is possible to produce a brain organoid in which the accumulation of the phosphorylated 3-repeat tau protein and the phosphorylated 4-repeat tau protein are accelerated. The culturing in the step 5 is preferably a suspension culture.

Examples of the method of dispersing a brain organoid include the same treatment as that in the dispersion of the mhPSCs before carrying out the expansion culture of the mhPSCs described above. The brain organoid is separated by dispersion into a cell population of 100 or less, preferably a cell population of 50 or less, and more preferably single cells, whereby a dispersion is formed.

The cell aggregate formed by the aggregation of the brain organoid dispersion exhibits a state in which two or more cells, which are the brain organoid dispersion, adhere to each other to form an aggregate. Examples of the method of forming the cell aggregate formed by the aggregation of the brain organoid dispersion include a method of carrying out suspension culture on the brain organoid dispersion in the culture medium 1 used in the step 1. The culture period of this suspension culture is usually 1 day or more, preferably 3 to 14 days, and more preferably 4 to 12 days.

In addition, this suspension culture is carried out in an environment in which the temperature is usually 30° C. to 50° C., preferably 32° C. to 48° C., and more preferably 34° C. to 46° C., and the carbon dioxide content rate is usually 1% by volume to 15% by volume, preferably 2% by volume to 14% by volume, and more preferably 3% by volume to 13% by volume.

The tau protein aggregate refers to an aggregate in which at least one kind or two or more kinds selected from the tau protein, a fragment of the tau protein, a recombinant tau protein, and a fragment of the recombinant tau protein are aggregated.

Among these, it is preferably a tau protein aggregate containing a recombinant tau protein or a fragment of the recombinant tau protein. In addition, the tau protein aggregate can contain an oligomer or filament of the tau protein or recombinant tau protein. Examples of the filament thereof include a paired helical filament and a straight filament.

The MAPT gene mutation encoding a recombinant tau protein is preferably at least one or more base sequence mutations in the exon 9 to the exon 13.

Examples of thereof include a base sequence mutation in the exon 9, such as a base sequence mutation encoding an amino acid mutation of K257V, K257T, I260V, L266V, or G272V; a base sequence mutation in the exon 10, such a base sequence mutation encoding an amino acid mutation of N279K, ΔK280, L284L, N296N, N296H, ΔN296, P301L, P301S, P301T, G303V, S305N, or S305S; a base sequence mutation in the exon 11, such as a base sequence mutation encoding an amino acid mutation of L315L, L315R, S320Y, S310F; a base sequence mutation in the exon 12, such as a base sequence mutation encoding an amino acid mutation of V337M, E342V, G335V, G335S, Q336R, or K369I; and a base sequence mutation in the exon 13, such as a base sequence mutation encoding an amino acid mutation of G389R or R406W. Among these, a base sequence mutation of the exon 10 is preferable, where P301L is preferable.

Culture is carried out in the presence of the tau protein aggregate, usually at 0.0005 ng to 0.4 ng, preferably 0.001 ng to 0.2 ng, and more preferably 0.002 ng to 0.1 ng, per one cell contained in the brain organoid dispersion or the cell aggregate formed by the aggregation of the dispersion.

The culture of the step 5 is preferably carried out in the presence of a phosphorylation-accelerating reagent. As the phosphorylation-accelerating reagent, an accelerating reagent generally called a transfection reagent can be used. As will be described later in Examples, the addition of a transfection reagent makes it possible to accelerate the phosphorylation (and the misfolding) of the tau protein.

Examples of the phosphorylation-accelerating reagent include EFFECTENE® Transfection Reagent (a nonliposomal lipid reagent for DNA transfection into a broad range of cell types) (catalog number "301425", QIAGEN N.V.), TRANSFAST™ Transfection Reagent (catalog number "E2431", Promega Corporation), TfxTM-20 Reagent (catalog number "E2391", Promega Corporation), SUPERFECT™ Transfection Reagent (catalog number "301305" QIAGEN N.V.), POLYFECT® Transfection Reagent (consists of dendrimer molecules of a defined spherical architecture with branches radiating from a central core) (catalog number "301105", QIAGEN N.V.), LIPOFECTAMINE™ (cationic-lipid transfection reagents) 2000 Reagent (catalog number "11668-019", Thermo Fisher Scientific, Inc.), LIPOFECTAMINE™ 3000 Reagent (catalog number "L3000015", Thermo Fisher Scientific, Inc.), JETPEI® (transfection reagent is a linear polyethylenimine derivative) (x4) conc. (catalog number "101-30", Polyplus-transfection SA), and ExGen 500 (catalog number "R0511", Fermentas).

The amount of the phosphorylation-accelerating reagent is preferably the same as the mass of the tau protein aggregate or ±90% thereof.

The culture medium that is used in the culture of the step 5 is preferably a culture medium containing no ECM. Examples of the culture medium containing no ECM include the same culture medium as the culture medium 3.

The culture period of the step 5 is usually 0.1 to 14 days, preferably 0.3 to 7 days, and more preferably 0.5 to 2 days. The culture of the step 5 is carried out in an environment in which the temperature is usually 30° C. to 50° C., preferably 32° C. to 48° C., and more preferably 34° C. to 46° C., and the carbon dioxide content rate is usually 1% by volume to 15% by volume, preferably 2% by volume to 14% by volume, and more preferably 3% by volume to 13% by volume.

The culture vessel that is used in the culture of the step 5 is preferably a cell non-adhesive culture vessel. The details of the cell non-adhesive culture vessel are the same as those in the step 1.

It is possible to provide a step 6 of further culturing the culture preparation formed by the culture of the step 5 in a culture medium containing no ECM. The step 6 can be carried out according to the same method as the step 3.

(Brain Organoid)

The brain organoid of the present embodiment can be produced by the production method for a brain organoid of the present embodiment, and it has a misfolded 3-repeat tau protein and a misfolded 4-repeat tau protein. Since misfolding is accelerated by phosphorylation or the like, the brain organoid of the present embodiment preferably has a phosphorylated 3-repeat tau protein and a phosphorylated 4-repeat tau protein.

An anti-MC1 antibody specifically binds to a misfolded 3-repeat tau protein and a misfolded 4-repeat tau protein. As a result, the presence of the misfolded 3-repeat tau protein and the misfolded 4-repeat tau protein can be checked by the detection by immunostaining with an anti-MC1 antibody or the like. The misfolded 3-repeat protein and the misfolded 4-repeat protein are conceived to have been phosphorylated.

In the brain organoid of the present embodiment, the detection signal intensity of the phosphorylated 4-repeat tau protein shown by Western blotting is 0.1 or more, preferably 0.3 or more, and more preferably 0.5 to 3, with respect to the detection signal intensity of 1 of the phosphorylated 3-repeat tau protein. The detection signal intensity is the luminescence intensity and fluorescence intensity exhibited by the reaction with an anti-PHF1 antibody.

The tau protein in the human brain is expressed, by alternative splicing, as six kinds of isoforms consisting of 352 to 441 amino acids, having molecular weights different from each other.

Examples of the six kinds of isoforms include a 0N3R tau protein (352 amino acids, NCBI accession number: NP_058525.1, NM_016841.4, or the like), a 0N4R tau protein which has the exons 2 and 3 (383 amino acids, NCBI accession number: NP_058518.1, NM_016834.4, or the like), a 1N3R tau protein having the exon 2 (381 amino acids, NCBI accession number: NP_001190180.1, NM_001203251.1, or the like), a 1N4R tau protein having the exon 2 (412 amino acids, NCBI accession number: NP_001116539.1, NM_001123067.3, or the like), a 2N3R tau protein having the exons 2 and 3 (410 amino acids, NCBI accession numbers: NP_001190181.1, NM_001203252.1, or the like), and a 2N4R tau protein having the exons 2 and 3 (441 amino acids, NCBI accession numbers: NP_005901.2, NM_005910.5, or the like).

The phosphorylated 4-repeat tau protein contained in the brain organoid of the present embodiment preferably includes a phosphorylated 0N4R tau protein, and the phosphorylated 3-repeat tau protein preferably includes a phosphorylated 0N3R tau protein.

[Drug Efficacy Evaluation Method]

A drug efficacy evaluation method of the present embodiment includes a step of bringing the above-described brain organoid into contact with a test substance (hereinafter, also referred to as a "step A"), and a step of examining an effect of the test substance on the brain organoid (hereinafter, also referred to as a "step B").

In the step A, examples of the test substance include a natural compound library, a synthetic compound library, an existing drug library, and a metabolite library. The existing drugs include, for example, AZD2858 and a methylthioninium chloride hydrate. In addition, a new drug can be used as the test substance.

In the step B, the effect of the test substance on the brain organoid can be examined or evaluated by Western blotting, ELISA, or immunostaining.

Further, before the step A, it is possible to provide a step of transplanting the brain organoid into the brain of a mammal (hereinafter, also referred to as a "step a"). In a case where the step a is provided, the drug efficacy of the test substance can be evaluated in an environment similar to that of a living body suffering from Alzheimer's disease.

EXAMPLES

Hereinafter, the present embodiment will be described in more detail based on Examples. However, the present embodiment is not limited to these Examples. It is to be noted that all experiments were carried out based on the ethics research plan approved by the Ethics Committee, Keio University School of Medicine.

Experimental Example 1

(Preparation of hiPSCs (mhiPSCs) Into which Modified MAPT Gene has been Introduced)

Using a guide RNA design software "CRISPRdirect" for genome editing, a guide RNA for targeting a target sequence of the MAPT gene was designed.

An oligonucleotide encoding the designed guide RNA was synthesized, and this oligonucleotide was inserted into the BbsI site of pSpCas9(BB)-2A-Puro (PX459) V2.0, which is an all-in-one vector for expressing both a Cas9 protein and a guide RNA.

A vector in which 1.5 kb on the 5' side as the 5' arm and 4 kb on the 3' side as the 3' arm, in the vicinity of the target sequence of the MAPT gene, had been ligated to a puromycin-resistant cassette sandwiched by piggyBac inverted terminal repeats was used as a targeting vector. The targeting vector had a base mutation in the exon 10, encoding amino acid mutations of N279K and P301S of the MAPT gene, and a mutation of E10+16 in the intron 10.

Next, 10 μg of the pSpCas9(BB)-2A-Puro (PX459) V2.0 plasmid and 10 μg of the targeting vector were introduced into 1 million hiPSCs (PChiPS771 strain, Lot No.: A01QM28, manufactured by ReproCELL Inc.) by an electroporation method using a NEPA21 electroporator (Nepa Gene Co., Ltd.).

From the 2nd to the 12th day after the start of gene introduction, the selection was carried out with puromycin. Next, puromycin-resistant colonies were selected and subjected to genotyping by genomic DNA extraction and PCR.

Next, a negative selection was carried out in order to remove the puromycin-resistant cassette, and colonies from which the puromycin-resistant cassette was removed were selected. The genomic DNA was extracted from the obtained colonies with a commercially available kit (product name: "DNEASY® Blood & Tissue Kit", QIAGEN N.V.), and then it was confirmed by the electrophoresis after PCR amplification that the puromycin cassette was removed. In addition, using the extracted genomic DNA, it was confirmed by the Sanger sequence analysis that the modified MAPT gene was included, and then mhiPSCs were obtained.

[Experimental Example 2]

(Expansion Culture of mhiPSCs)

The mhiPSCs prepared in Experimental Example 1 were subjected to feeder-free culture. Specifically, the mhiPSCs were washed with phosphate-buffered saline (PBS) and then dispersed into single cells using TRYPLE™ Select (purified, animal-origin free cell dissociation enzymes that replace porcine trypsin) (manufactured by Thermo Fisher Scientific, Inc.). Subsequently, the dispersed mhiPSCs were seeded in a plastic culture dish coated with a human recombinant laminin fragment (product name: "iMatrix-511", manufactured by Nippi. Inc.) containing only the active site portion of laminin-511 and subjected to feeder-free culture in a STEMFIT® AK02N culture medium (manufactured by Ajinomoto Co., Inc.) in the presence of Y27632 (a ROCK inhibitor, 10 μM). In a case where a 60 mm dish (for cell culture, manufactured by IWAKI & CO., LTD.) was used as the above plastic culture dish, the number of seeded cells of the hiPSCs dispersed into single cells was $3\times10^4$ cells/dish.

One day after seeding the cells, the culture medium was exchanged with a StemFit AK02N culture medium containing no Y27632. After that, the culture medium was exchanged with the STEMFIT® AK02N culture medium containing no Y27632 one time every 1 to 2 days. Then, 6 days after seeding the cells, the confluency thereof was 80%.

Experimental Example 3

(Expansion Culture of hiPSCs)

hiPSCs were subjected to expansion culture according to the same operation as in Experimental Example 2 except that in Experimental Example 2, wild-type hiPSCs (PChiPS771 strain, manufactured by ReproCELL Inc.) were used instead of the mhiPSCs.

Experimental Example 4 to Experimental Example 7

(Brain Organoid Production 1)

Table 1 below shows the composition of the culture medium 1, Table 2 below shows the composition of the culture medium 2, and Table 3 below shows the composition of the culture medium 3. FIG. 1 is a schematic diagram showing an exchange schedule of a culture medium of a human brain organoid. In FIG. 1, "Day" indicates the number of culture days in a case where at the time of the start of suspension culture is set as the 0th day, "+" indicates that a culture medium has been added, "–" indicates that a culture medium has not been added, "BMPi" indicates an inhibitor of a BMP signal transduction pathway, "TGF-βi" indicates an inhibitor of a TGF-β signal transduction pathway, "ECM" indicates an extracellular matrix component, and "Wnt" indicates a Wnt signaling enhancing agent.

TABLE 1

| | Component | Content |
|---|---|---|
| Basal culture medium | StemFit AK02N (product name, manufactured by Ajinomoto Co., Inc.) | — |
| Culture medium supplement | MEM Non-Essential Amino Acids Solution (100X) (product name, manufactured by Thermo Fisher Scientific, Inc.) | An amount that gives a dilution in concentration by 200-fold with respect to the basal culture medium |
| | Penicillin-Streptomycin Mixed Solution sterility tested, mycoplasma tested, and endotoxin tested (product name, manufactured by Nacalai Tesque, Inc.) | An amount that gives a dilution in concentration by 100-fold with respect to the basal culture medium |
| | DMEM, low glucose, GlitaMAX (registered trade name) Supplement, pyruvate (product name, manufactured by Thermo Fisher Scientific, Inc.) | An amount that gives a dilution in concentration by 100-fold with respect to the basal culture medium |
| | 2-mercaptoethanol (product name, manufactured by Thermo Fisher Scientific, Inc.) | An amount that gives a dilution in concentration by 1,000-fold with respect to the basal culture medium |

TABLE 1-continued

| | Component | Content |
|---|---|---|
| BMP inhibitor | Dorsomorphin | Final concentration: 2 μM |
| TGF-β inhibitor | A83-01 | Final concentration: 2 μM |

TABLE 2

| | Component | Content |
|---|---|---|
| Basal culture medium | DMEM/F-12, HEPES (product name, manufactured by Thermo Fisher Scientific, Inc.) | — |
| Culture medium supplement | MEM Non-Essential Amino Acids Solution (100X) (product name, manufactured by Thermo Fisher Scientific, Inc.) | An amount that gives a dilution in concentration by 200-fold with respect to the basal culture medium |
| | Penicillin-Streptomycin Mixed Solution sterility tested, mycoplasma tested, and endotoxin tested (product name, manufactured by Nacalai Tesque, Inc.) | An amount that gives a dilution in concentration by 100-fold with respect to the basal culture medium |
| | DMEM, low glucose, GlitaMAX (registered trade name) Supplement, pyruvate (product name, manufactured by Thermo Fisher Scientific, Inc.) | An amount that gives a dilution in concentration by 100-fold with respect to the basal culture medium |
| Wnt signal-enhancing agent | Wnt-3a, Human, Recombinant (product name, manufactured by R&D Systems) | Final concentration: 4 ng/mL |
| | CHIR99021 | Final concentration: 1 μM |
| TGF-β inhibitor | SB-431542 | Final concentration: 2 μM |
| Extracellular matrix | Matrigel | Final concentration: 30% by volume |

TABLE 3

| | Component | Content |
|---|---|---|
| Basal culture medium | DMEM/F-12, HEPES (product name, manufactured by Thermo Fisher Scientific, Inc.) | — |
| Culture medium supplement | N-2 Supplement (100X) (product name, manufactured by Thermo Fisher Scientific, Inc.) | An amount that gives a dilution in concentration by 200-fold with respect to the basal culture medium |
| | B-27(R) Serum-free Supplement (product name, manufactured by Thermo Fisher Scientific, Inc.) | An amount that gives a dilution in concentration by 100-fold with respect to the basal culture medium |
| | MEM Non-Essential Amino Acids Solution (100X) (product name, manufactured by Thermo Fisher Scientific, Inc.) | An amount that gives a dilution in concentration by 200-fold with respect to the basal culture medium |
| | 2-mercaptoethanol (product name, manufactured by Thermo Fisher Scientific, Inc.) | An amount that gives a dilution in concentration by 1,000-fold with respect to the basal culture medium |
| | Insulin Solution, Human, recombinant (product name, manufactured by FUJIFILM Wako Pure Chemical Corporation) | Final concentration: 2.5 μg/mL |

The mhiPSCs obtained in Experimental Example 2 were subjected to a cell dispersion liquid treatment by using TRYPLE™ Select (product name, manufactured by Thermo Fisher Scientific, Inc.) and further dispersed into single cells by a pipetting operation. The dispersed mhiPSCs were seeded in a cell non-adhesive 96-well plate (product name: “PRIMESURFACE® 96V bottom plate”, manufactured by Sumitomo Bakelite Co., Ltd.) so that the cell density was $1\times10^4$ cells/well in a culture medium 1 of 100 μL/well, and then subjected to suspension culture for 7 days at 37° C. and a carbon dioxide concentration 5% by volume in a container.

On the 7th day after the start of suspension culture, 230 μL of the culture medium 1 was removed from each well. Subsequently, the culture medium 2 was added at 150 μL/well, and suspension culture was carried out for 7 days with stirring at 37° C. and a carbon dioxide concentration of 5% by volume in a container.

On the 14th day after the start of suspension culture, the contents of each well were transferred to a 50 mL FALCON® (registered trade name) conical tube (manufactured by Corning Incorporated) containing 10 mL of PBS. Subsequently, mixing with inversion was carried out 5 times, the culture medium 2 was removed by removing the supernatant, and the cell aggregates were collected. Thirty collected cell aggregates and 30 mL of the culture medium 3 were added to a 30 mL single-use bioreactor (ABLE Corporation) and subjected to suspension culture with stirring. The culture medium was exchanged every 4 days. Brain organoids were collected on the 56th day after the start of suspension culture, on the 91st day after the start of suspension culture, on the 140th day after the start of suspension culture, and on the 175th day after the start of suspension culture, whereby each of the brain organoids of Experimental Example 4 to Experimental Example 7 was obtained.

Experimental Example 8 to Experimental Example 11

(Brain Organoid Production 2)

Each of the brain organoids of Experimental Example 8 to Experimental Example 11 was obtained according to the same operations as in Experimental Example 4 to Experimental Example 7 except that in Experimental Example 4 to Experimental Example 7, the wild-type hiPSCs obtained in Experimental Example 3 were used instead of the mhiPSCs obtained in Experimental Example 2.

[Experimental Example 12]

(mRNA Expression Level Analysis of 4-repeat tau protein)

The total RNA of the brain organoid of each of Experimental Example 4 to Experimental Example 11 was extracted using a commercially available kit (product name: "RNEASY® PlusMini Kit", QIAGEN N.V.). In addition, the concentration of the total RNA was measured using NANODROP® spectrophotometer (product name, Thermo Fisher Scientific, Inc.). Subsequently, the total RNA was reverse transcribed with RT Master Mix (product name, TOYOBO Co., Ltd.) and a Nuclease-free water to synthesize cDNA.

Figure 2:
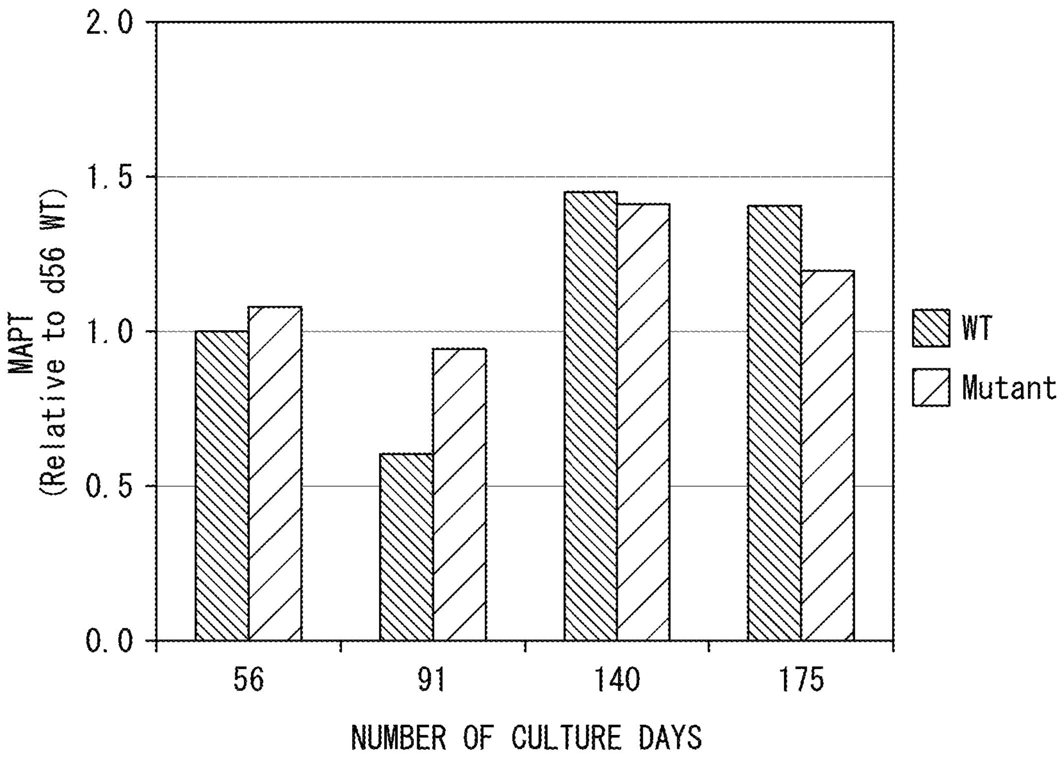
FIG. 2 is a graph showing results of quantitative RT-PCR in Experimental Example 12.
Figure 3:
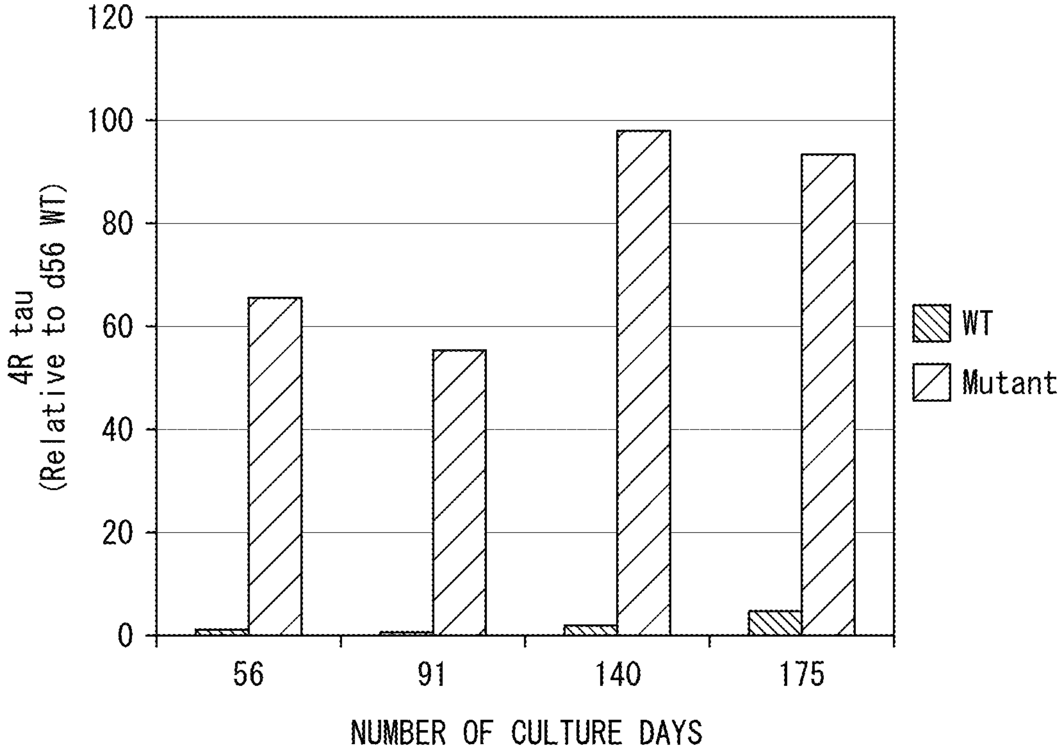
FIG. 3 is a graph showing results of the quantitative RT-PCR in Experimental Example 12.

Premix Ex Taq (product name, Takara Bio Inc.) and ROX Reference Dye II (product name, Takara Bio Inc.) were added to the above cDNA to prepare a reaction solution. Subsequently, the quantitative RT-PCR (qPCR) analysis of the above reaction solution was carried out using a real-time PCR system (product name: "ViiA7", Thermo Fisher Scientific, Inc.), and the expression level of mRNA of the MAPT gene and the expression level of mRNA of the 4-repeat tau were each quantified. A sense primer (SEQ ID NO: 1) and an antisense primer (SEQ ID NO: 2) were used for the amplification of the cDNA of the MAPT gene. Further, a sense primer (SEQ ID NO: 3) and an antisense primer (SEQ ID NO: 4) were used for the amplification of the cDNA of the 4-repeat tau. The results are shown in FIG. 2 and FIG. 3. Further, a summary of the measurement results is shown in Table 4 below.

FIG. 2 shows the measurement results of the expression level of mRNA of the MAPT gene, where the expression level is shown as a relative value in a case where the expression level of mRNA of the MAPT gene in the brain organoid obtained in Experimental Example 4 was set as 1. In addition, FIG. 3 shows the measurement results of the expression level of mRNA of the 4-repeat tau protein, where the expression level is shown as a relative value in a case where the expression level of mRNA of the 4-repeat tau protein in the brain organoid obtained in Experimental Example 8 was set as 1.

TABLE 4

| | Expression level of mRNA of MAPT gene | Expression level of mRNA of 4-repeat tau |
|---|---|---|
| Experimental Example 4 | 1.1 | 66 |
| Experimental Example 5 | 0.9 | 55 |
| Experimental Example 6 | 1.4 | 98 |
| Experimental Example 7 | 1.2 | 93 |
| Experimental Example 8 | 1.0 | 1.0 |
| Experimental Example 9 | 0.6 | 0.5 |
| Experimental Example 10 | 1.5 | 1.9 |
| Experimental Example 11 | 1.4 | 4.8 |

Experimental Example 13

(Measurement of Isoforms of Tau Protein by Western Blotting Method)

Isoforms of the tau proteins were observed by the Western blotting method. A RIPA buffer was added to the brain organoid obtained in Experimental Example 7 and the brain organoid obtained in Experimental Example 11, followed by ultrasonic disruption on ice. Subsequently, the obtained cell disruption solution was allowed to stand on ice for 60 minutes. Subsequently, the cell disruption solution was centrifuged at 4° C. and 100,000×g, whereby the supernatant was collected. Subsequently, the protein concentration in the supernatant was measured using the bicinchoninic acid assay kit. Subsequently, λ phosphatase was added to the supernatant, followed by a reaction at 30° C. for 3 hours. Subsequently, equal amounts of each supernatant were applied to two wells, SDS-polyacrylamide gel electrophoresis (PAGE) was carried out, and the proteins were transferred to a polyvinylidene fluoride membrane (hereinafter, a "PVDF membrane").

Subsequently, the PVDF membrane was immersed in a PVDF Blocking reagent (product name, TOYOBO Co., Ltd.), blocked at room temperature for 1 hour, and then reacted at 4° C. overnight with a mouse anti-tau 5 antibody reaction solution diluted by 1,000-fold with Can Get Signal Immunoreaction Enhancer Solution 1 (product name, TOYOBO Co., Ltd.). Subsequently, the PVDF membrane was washed 3 times with a TBST buffer and reacted for 1 hour at room temperature with a horseradish peroxidase (hereinafter referred to as "HRP") -labeled anti-mouse IgG antibody reaction solution diluted by 1,000-fold with Can Get Signal Immunoreaction Enhancer Solution 1 (product name, TOYOBO Co., Ltd.).

Figure 4:
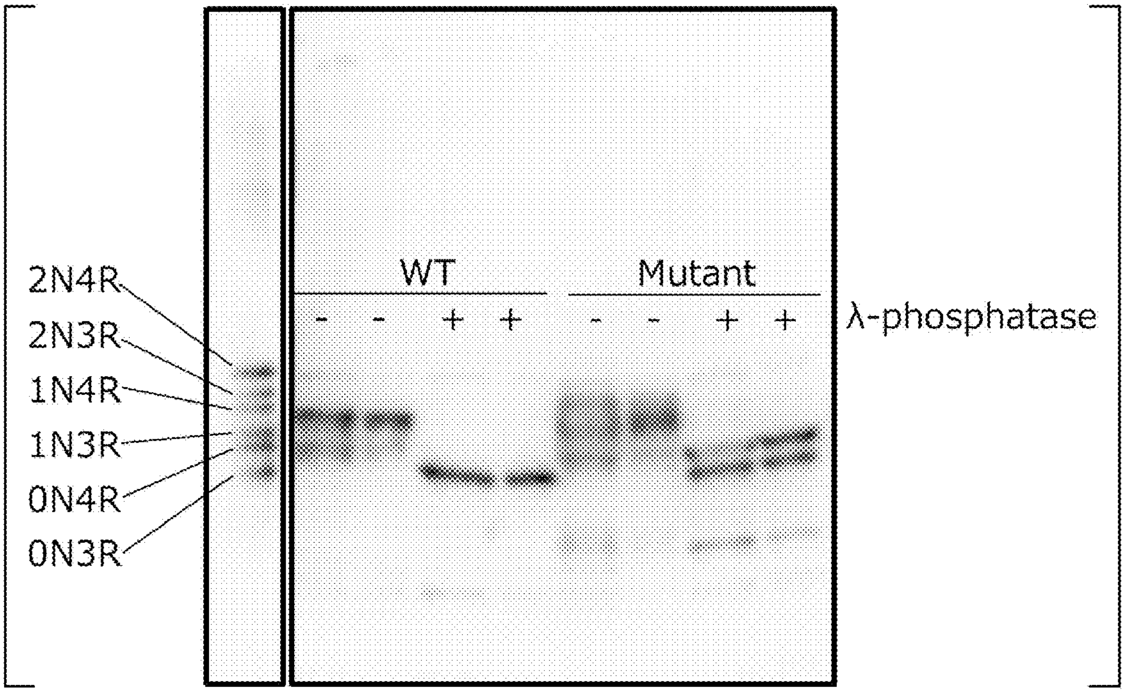
FIG. 4 is a photographic image showing results of Western blotting in Experimental Example 13.

Subsequently, after washing 3 times with a TBST buffer, CLARITY™ Western ECL Substrate (product name, Bio-Rad Laboratories, Inc.) was applied on the PVDF membrane and allowed to stand for 2 minutes. Subsequently, bands of the isoforms of the tau protein were detected using a luminescence detection device (product name: "AMERSHAM™ Imager 600", GE Healthcare). FIG. 4 is a photographic image showing results of the Western blotting.

In FIG. 4, "WT" indicates that the result has been obtained from the brain organoid obtained in Experimental Example 11, "Mutant" indicates that the result has been obtained from the brain organoid obtained in Experimental Example 7, "+" indicates that the result has been obtained with a reaction with λ phosphatase, and"−" indicates that the result has been obtained without a reaction with λ phosphatase. In addition, the leftmost lane in FIG. 4 is a marker for each tau protein isoform. In addition, Table 5 below shows the intensity (in terms of relative value) of the detection signal of the 4-repeat tau protein (0N4R) in a case where the detection signal of the 3-repeat tau protein (0N3R) in the brain organoid obtained in Experimental Example 7 was set as 1.

TABLE 5

| | Intensity of detection signal of 4-repeat tau protein (0N4R) (relative value) |
|---|---|
| Experimental Example 7 | 1.0 |
| Experimental Example 11 | 0 |

Experimental Example 14

(Measurement of Phosphorylated Tau Protein by Western Blotting Method)

The expression of phosphorylated tau protein was measured by the Western blotting method. A RIPA buffer containing a protease inhibitor and a phosphatase inhibitor was added to the brain organoid obtained in Experimental Example 7 and the brain organoid obtained in Experimental Example 11, followed by ultrasonic disruption on ice. Subsequently, the obtained cell disruption solution was allowed to stand on ice for 60 minutes. Subsequently, the cell disruption solution was centrifuged at 4° C. and 100,000×g, whereby the supernatant was collected. Subsequently, the protein concentration in the supernatant was measured using the bicinchoninic acid assay kit. Subsequently, the supernatant was applied to a well, SDS-PAGE was carried out, and the proteins were transferred to a PVDF membrane.

Subsequently, the PVDF membrane was immersed in a PVDF Blocking reagent (product name, TOYOBO Co., Ltd.), blocked at room temperature for 1 hour, and then reacted at 4° C. overnight with a mouse anti-PHF1 antibody reaction solution diluted by 1,000-fold with Can Get Signal Immunoreaction Enhancer Solution 1 (product name, TOYOBO Co., Ltd.). It is to be noted that the anti-PHF1 antibody is an antibody that recognizes the phosphorylated serine at 396th residue of the tau protein and the phosphorylated serine at 404th residue thereof.

Subsequently, the cells were washed 3 times with TBST buffer and reacted with an HRP-labeled anti-mouse IgG antibody reaction solution diluted 1000-fold with Can Get Signal Immunoreaction Enhancer Solution 1 (product name, TOYOBO Co., Ltd.) for 1 hour at room temperature.

Figure 5:
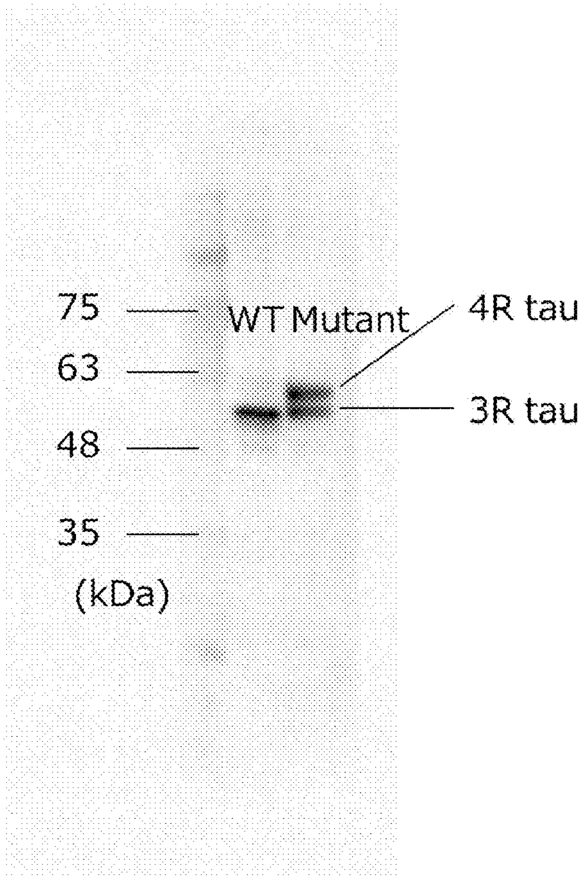
FIG. 5 is a photographic image showing results of the Western blotting in Experimental Example 14.

Subsequently, after washing 3 times with a TBST buffer, ECL Prime Western Blotting Detection Reagent (product name, GE Healthcare) was added onto the PVDF membrane and allowed to stand for 2 minutes. Subsequently, the luminescence was detected using a luminescence detection device (product name: "Amersham Imager 600", GE Healthcare). Subsequently, the signal intensity of the obtained band was detected. FIG. 5 is a photographic image showing results of the Western blotting.

In FIG. 5, "WT" indicates that the result has been obtained from the brain organoid obtained in Experimental Example 11, "Mutant" indicates that the result has been obtained from the brain organoid obtained in Example 7, "3R tau" indicates that the band is a band of the phosphorylated 3-repeat tau protein, and "4R tau" indicates that the band is a band of the phosphorylated 4-repeat tau protein. In addition, Table 6 below shows the intensity (in terms of relative value) of the detection signal of the phosphorylated 4-repeat tau protein in a case where the detection signal of the phosphorylated 3-repeat tau protein in the brain organoid obtained in Experimental Example 7 was set as 1.

TABLE 6

| | Intensity of detection signal of phosphorylated 4-repeat tau protein manufactured by (relative value) |
|---|---|
| Experimental Example 7 | 1.2 |
| Experimental Example 11 | 0 |

Experimental Example 15

(Immunostaining of Brain Organoid with MC1 Antibody and RTM38 Antibody)

The misfolded 3-repeat tau protein and the misfolded 4-repeat tau protein contained in the brain organoid were evaluated by immunostaining using an MC1 antibody. In addition, the tau protein was evaluated by immunostaining using an RTM38 antibody (FUJIFILM Wako Pure Chemical Corporation).

Figure 6A:
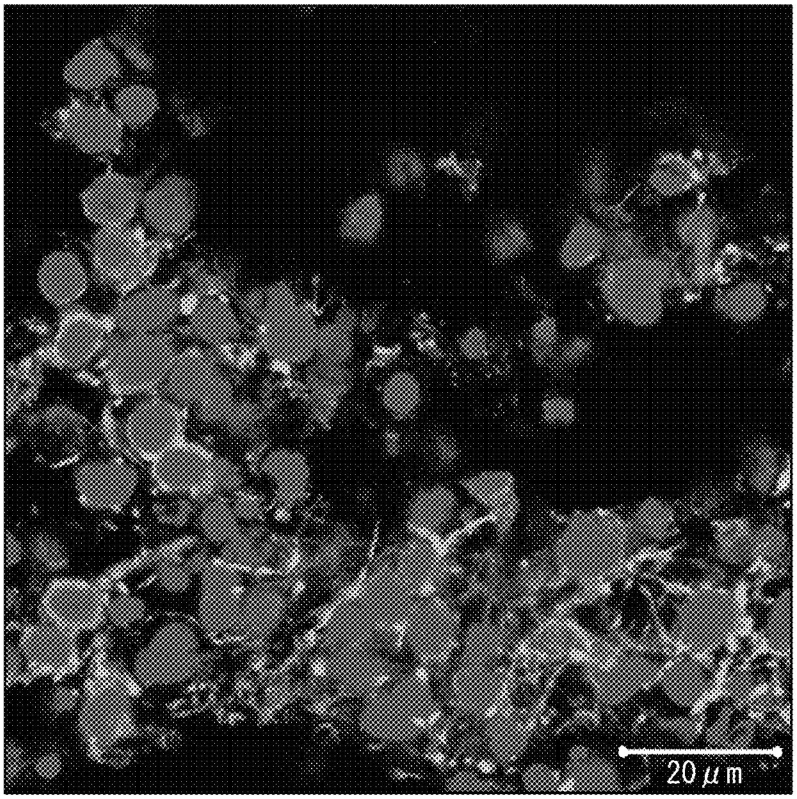
FIG. 6A is a photomicrographic image showing result of fluorescent immunostaining in Experimental Example 15.
Figure 6B:
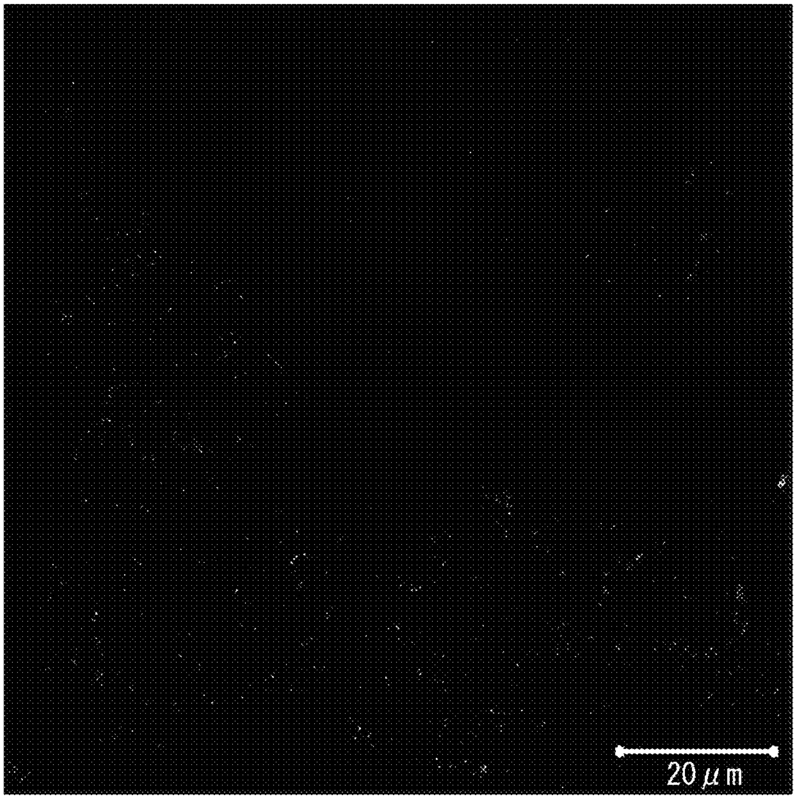
FIG. 6B is a photomicrographic image showing result of fluorescent immunostaining in Experimental Example 15.

The presence of the misfolded tau protein was evaluated by fluorescent immunostaining of slices of the brain organoid obtained in Experimental Example 7 and the brain organoid obtained in Experimental Example 11. In addition, the nuclei were also stained with 4',6-diamidino-2-phenylindole (DAPI). FIG. 6A and FIG. 6B are fluorescent immunostaining images of the brain organoid obtained in Experimental Example 7, and FIG. 7A and FIG. 7B are fluorescent immunostaining images of the brain organoid obtained in Experimental Example 11.

FIG. 6A is an image obtained by merging the fluorescent staining image with DAPI, the fluorescent staining image with the MC1 antibody, and the fluorescent staining image with the RTM38 antibody, which were obtained from the brain organoid obtained in Experimental Example 7. FIG. 6B is a fluorescent staining image with the MC1 antibody in the same visual field as in FIG. 6A.

Figure 7A:
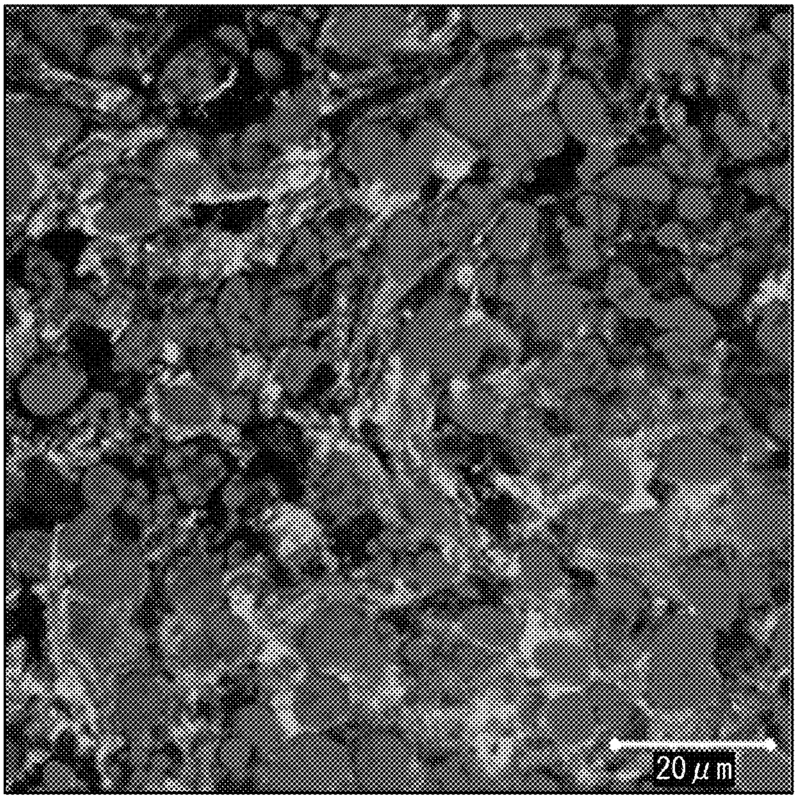
FIG. 7A is a photomicrographic image showing results of the fluorescent immunostaining in Experimental Example 15.
Figure 7B:
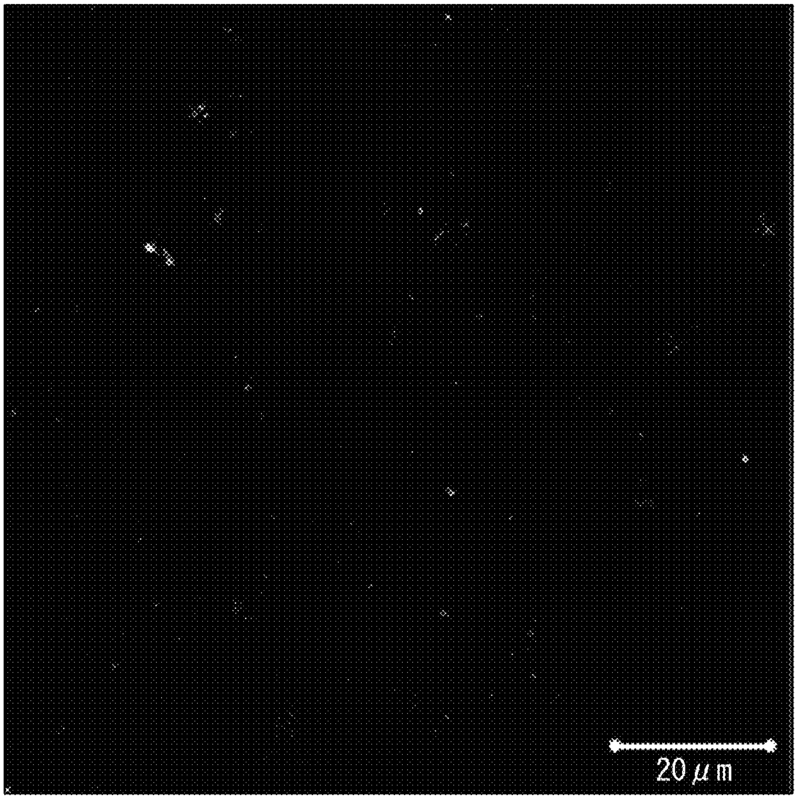
FIG. 7B is a photomicrographic image showing results of the fluorescent immunostaining in Experimental Example 15.

FIG. 7A is an image obtained by merging the fluorescent staining image with DAPI, the fluorescent staining image with the MC1 antibody, and the fluorescent staining image with the RTM38 antibody, which were obtained from the brain organoid obtained in Experimental Example 11. FIG. 7B is a fluorescent staining image with the MC1 antibody in the same visual field as in FIG. 7A.

As a result of the above, it was confirmed that in the brain organoid obtained in Experimental Example 7 and the brain organoid obtained in Experimental Example 11, the signal of the MC1 antibody could not be confirmed, and thus the misfolded tau protein was not present. However, the signal of the RTM38 antibody was confirmed, which indicates that the tau protein was expressed.

Experimental Example 16 to Experimental Example 19

(Brain Organoid Production Using Tau Protein Aggregate)

The mhiPSCs obtained in Experimental Example 2 were subjected to a cell dispersion liquid treatment by using TripLE Select (product name, manufactured by Thermo Fisher Scientific, Inc.) and further dispersed into single cells by a pipetting operation. The dispersed mhiPSCs were seeded in a cell non-adhesive 96-well plate (product name: "Prime Surface 96V bottom plate", manufactured by Sumitomo Bakelite Co., Ltd.) so that the cell density was $1\times10^4$ cells/well in the culture medium 1 of 100 μL/well, and then subjected to suspension culture for 7 days at 37° C. and a carbon dioxide concentration 5% by volume in a container.

On the 7th day after the start of suspension culture, 230 μL of the culture medium 1 was removed from each well. Subsequently, the culture medium 2 was added at 150 μL/well, and suspension culture was carried out for 7 days with stirring at 37° C. and a carbon dioxide concentration of 5% by volume in a container.

On the 14th day after the start of suspension culture, the contents of each well were transferred to a 50 mL FALCON® (registered trade name) conical tube (manufactured by Corning Incorporated) containing 10 mL of PBS. Subsequently, mixing with inversion was carried out 5 times, the culture medium 2 was removed by removing the supernatant, and the cell aggregates were collected. Thirty collected cell aggregates and 30 mL of the culture medium 3 were added to a 30 mL single-use bioreactor (ABLE Corporation) and subjected to suspension culture with stirring. The culture medium was exchanged every 4 days. The brain organoids were collected 10 weeks after the start of suspension culture.

The collected brain organoids were subjected to a cell dispersion liquid treatment by using TRYPLE™ Select (product name, manufactured by Thermo Fisher Scientific, Inc.) and further dispersed into single cells by a pipetting operation. The dispersed brain organoids were harvested in a cell non-adhesive 96-well plate (product name: "PRIMESURFACE® 96V bottom plate", manufactured by Sumitomo Bakelite Co., Ltd.) so that the cell density was $1\times10^4$ cells/well in a culture medium of 100 μL/well, and then subjected to suspension culture for one week at 37° C. and a carbon dioxide concentration 5% by volume in a container, whereby cell aggregates were formed.

Subsequently, to the culture medium 1, a fibril-type tau recombinant protein aggregate K18 type (product code: "#SPR-330", manufactured by StressMarq Biosciences Inc.) was added at 0.2 μg/well and a phosphorylation-accelerating reagent (product name: "LIPOFECTAMINE™ 3000" (manufactured by Thermo Fisher Scientific, Inc.) was added at 0.2 μL/well, and then suspension culture was carried out for 1 day at 37° C. and a carbon dioxide concentration of 5% by volume in a container.

The fibril-type tau recombinant protein aggregate K18 type is an aggregate in which fragments of a human recombinant tau protein having a mutation of P301L in the exon 10 of the human tau protein are aggregated. The amino acid sequence of the fragment of the recombinant tau protein contained in the fibril-type tau recombinant protein aggregate K18 type is shown in SEQ ID NO: 5.

Subsequently, the suspension culture preparation was collected from the well, the collected thirty cell aggregates and 30 mL of the culture medium 3 were added to a 30 mL single-use bioreactor ABLE Corporation) and subjected to suspension culture for 10 weeks with stirring, whereby brain organoids of Experimental Example 16 were obtained. The culture medium was exchanged every 4 days.

In addition, brain organoids of Experimental Example 17 to Experimental Example 19 were obtained under the conditions shown in Table 7 below. Each of the brain organoids was obtained in the same manner as in Experimental Example 16, except that in Experimental Example 17, the fibril-type tau recombinant protein aggregate K18 type and LIPOFECTAMINE™ 3000 were not used, except that in Experimental Example 18, the hiPSCs of Experimental Example 3 were used instead of the mhiPSCs of Experimental Example 2, and except that in Experimental Example 19, the fibril-type tau recombinant protein aggregate K18 type and LIPOFECTAMINE™ 3000 were not used and the hiPSCs of Experimental Example 3 were used instead of the mhiPSCs of Experimental Example 2.

TABLE 7

Figure 9:
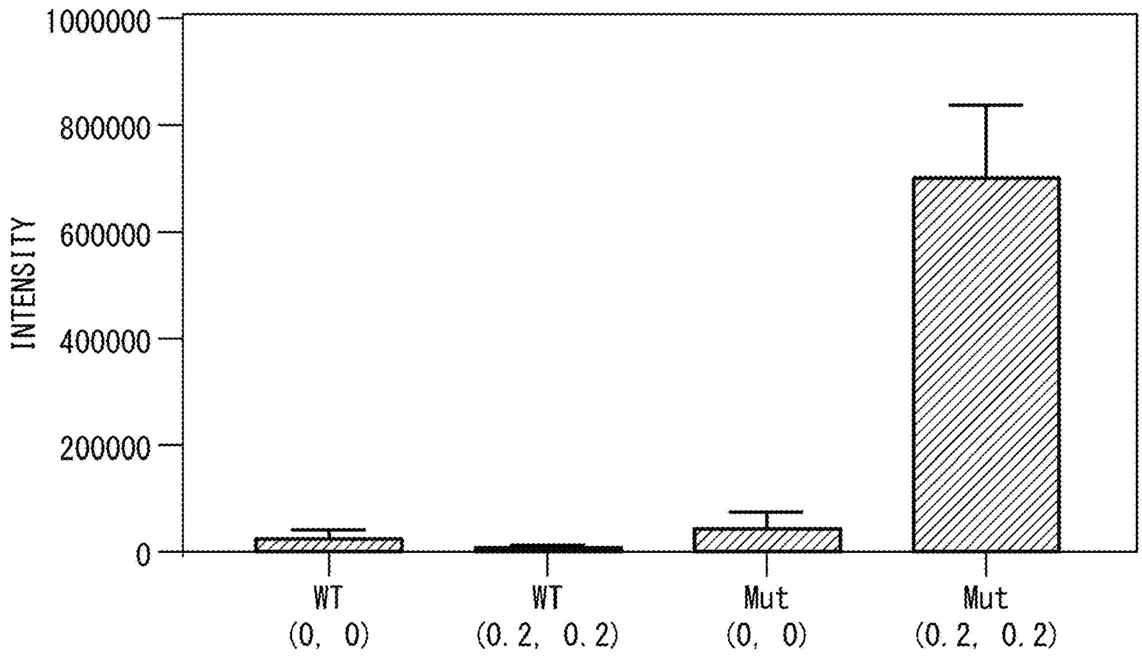
FIG. 9 is a graph showing results of quantifying the signal intensity (in terms of relative value) of an anti-MC1 antibody in Experimental Example 20.
Figure 10:
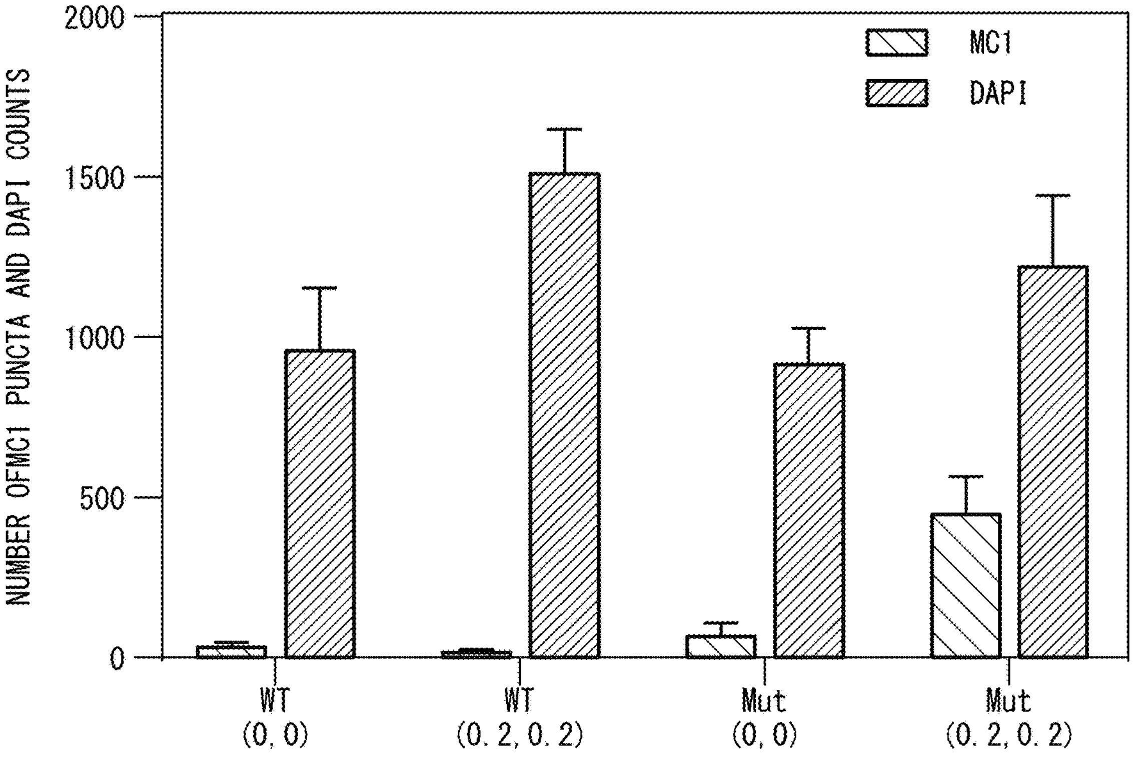
FIG. 10 is a graph showing results of calculating the number of nuclei (DAPI counts) and the number of granules (MC1 puncta) stained with an anti-MC1 antibody in a brain organoid in Experimental Example 20.
Figure 11:
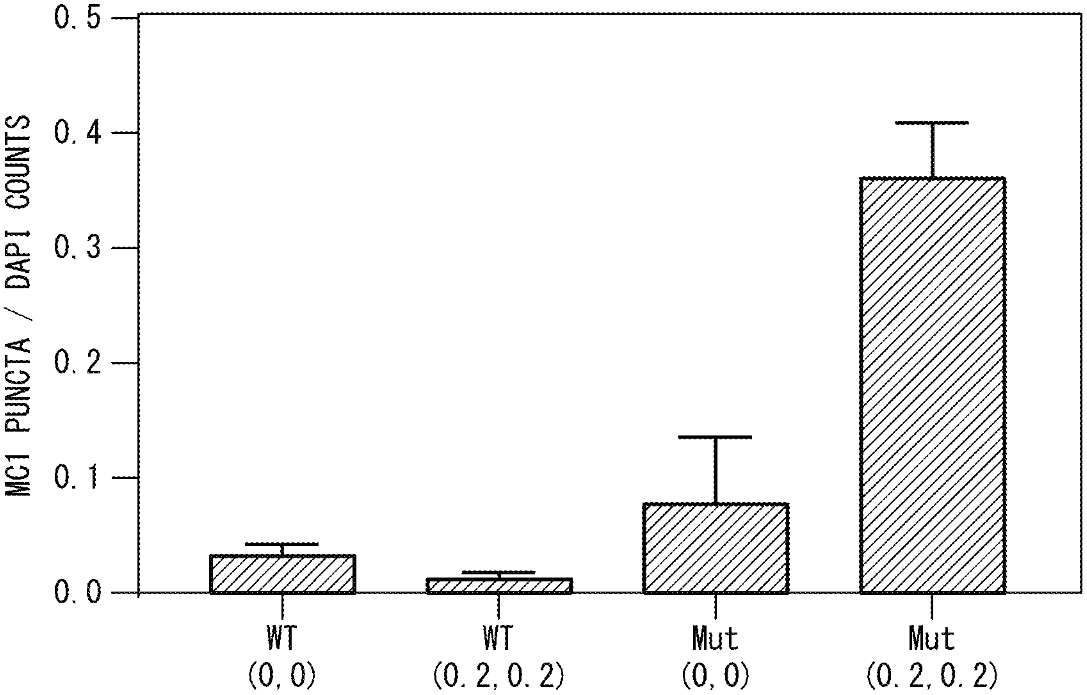
FIG. 11 is a graph showing results of calculating the number of granules stained with an anti-MC1 antibody per one cell (MC1 puncta/DAPI counts) in the brain organoid in Experimental Example 20.

| | Cell | Fibril-type tau recombinant protein aggregate K18 type | LIPOFECTAMINE™ name) 3000 | Notation in FIG. 9 to FIG. 11 |
|---|---|---|---|---|
| Experimental Example 16 | mhiPSC | 0.2 μg/well | 0.2 μg/well | Mut (0.2, 0.2) |
| Experimental Example 17 | mhiPSC | — | — | Mut (0, 0) |
| Experimental Example 18 | hiPSC | 0.2 μg/well | 0.2 μg/well | WT (0.2, 0.2) |
| Experimental Example 19 | hiPSC | — | — | WT (0, 0) |

Experimental Example 20

(Checking of Misfolding of Tau Protein in Brain Organoid Using Tau Protein Aggregate)

The presence of the misfolded 3-repeat tau protein and the misfolded 4-repeat tau protein contained in the brain organoid obtained in Experimental Example 16 to Experimental Example 19 were checked by immunostaining using an anti-MC1 antibody.

First, slices of the brain organoids obtained in Experimental Example 16 to Experimental Example 19 were prepared. Subsequently, each slice was immunostained with an anti-MC1 antibody. In addition, the nuclei were stained with DAPI at the same time. Subsequently, each slice was observed with a fluorescence microscope.

Figure 8:
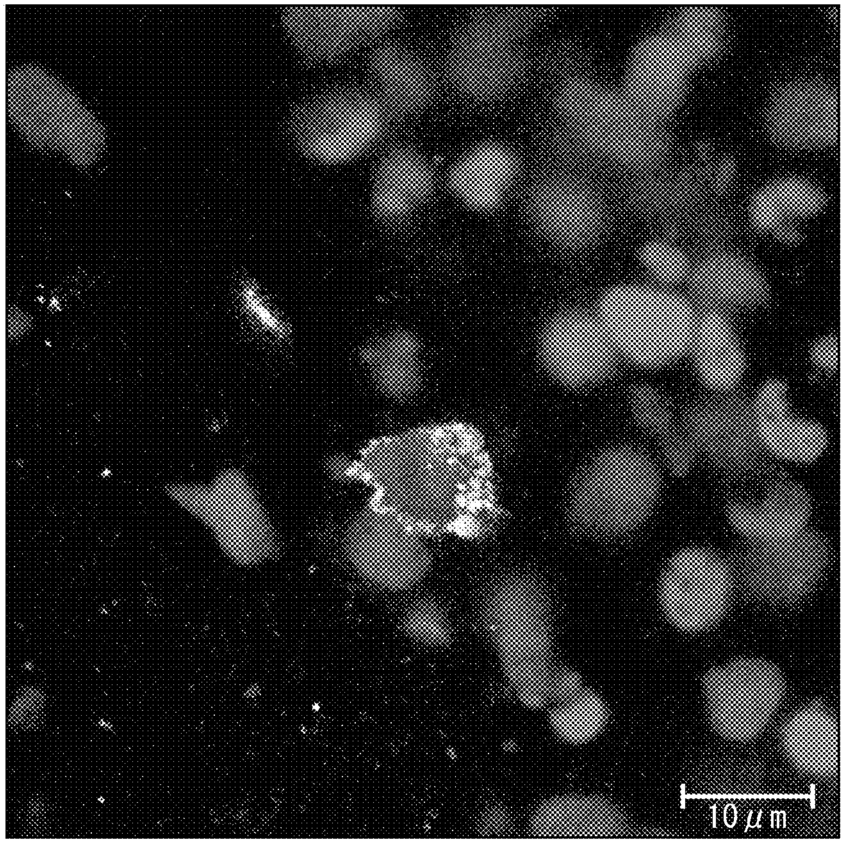
FIG. 8 is a photomicrographic image showing results of fluorescent immunostaining in Experimental Example 20.

FIG. 8 is a typical photomicrographic image showing a fluorescent immunostaining image of the brain organoid obtained in Experimental Example 16, which is an image obtained by merging the fluorescent staining image with DAPI and the fluorescent staining image with the MC1 antibody.

FIG. 9 is a graph showing results of quantifying the signal intensity (in terms of relative value) of the anti-MC1 antibody based on the fluorescent immunostaining images of the brain organoids obtained in Experimental Example 16 to Experimental Example 19. As a result of the above, it was revealed that in the brain organoid obtained in Experimental Example 16, the accumulation amount of the misfolded 3-repeat tau protein and the misfolded 4-repeat tau protein was remarkably large as compared with the brain organoids obtained in Experimental Example 17 to Experimental Example 19.

Subsequently, the fluorescent immunostaining images of the brain organoids obtained in Experimental Example 16 to Experimental Example 19 were subjected to image processing, and the number of nuclei stained with DAPI (DAPI counts) and the number of granules stained with the anti-MC1 antibody (MC1 puncta) were calculated. FIG. 10 is a graph showing the results. The number of nuclei stained with DAPI corresponds to the number of cells.

In addition, the number of granules stained with the anti-MC1 antibody (MC1 puncta/DAPI counts) per one cell was calculated by the image processing of the fluorescent immunostaining images of the brain organoids obtained in Experimental Example 16 to Experimental Example 19. FIG. 11 is a graph showing the results.

Image processing was carried out as follows. First, the background noise in the obtained fluorescent immunostaining image was cut. Subsequently, the image was corrected in accordance with the brightness of the background, and granules of DAPI and MC1 were identified by binarization. Subsequently, the gaps in the DAPI-positive regions and the MC1-positive regions were filled. Subsequently, DAPI-positive regions and MC1-positive regions having a size of a region (a diameter of a circle in a case of assuming a circle having the same area as the region) of 0.1 μm or less were removed. Subsequently, the number of remaining DAPI-positive regions (corresponding to the number of nuclei, that is, the number of cells) and the number of remaining MC1-positive regions (the number of granules stained with the anti-MC1 antibody) were measured.

INDUSTRIAL APPLICABILITY

According to the present invention, it is possible to provide a brain organoid in which a phosphorylated 3-repeat tau protein and a phosphorylated 4-repeat tau protein have accumulated and a production method thereof, as well as a drug efficacy evaluation method using the brain organoid.

The invention claimed is:

1. A method of making a brain organoid, comprising:

suspension culturing human pluripotent stem cells comprising a microtubule-associated protein tau (MAPT) gene that comprises an N279K mutation and a P301S mutation in exon 10 and an E10+16 mutation in intron 10 in a first culture media comprising an inhibitor of bone morphogenetic protein (BMP) signaling and an inhibitor of transforming growth factor β (TGF-β) family signaling to produce a first culture preparation;

suspension culturing the first culture preparation in a second culture media comprising a GSK-3β inhibitor, an inhibitor of transforming growth factor β (TGF-β) family signaling, and an extracellular matrix mixed therein to produce a second culture preparation; and culturing the second culture preparation in a third culture media that does not comprise extracellular matrix to produce a cultured brain organoid comprising a ratio of 4R phosphorylated tau/3R phosphorylated tau of at least 1.

2. The method of claim 1, wherein the inhibitor of a TGF-β family signal transduction pathway is one or more of A83-01, SB-431542, SB-505124, SB-525334, LY364947, SC-203294, SD-208, and SJN2511.

3. The method of claim 1, wherein the inhibitor of a BMP signal transduction pathway is one or more of chordin, noggin, follistatin, dorsomorphin, DMH1 and LDN193189.

4. The method of claim 1, wherein the GSK-3β inhibitor is at least one of CHIR99021, kenpaullone, and 6-bromoindirubin-3'-oxime.

5. The method of claim 1, wherein the inhibitor of a TGF-β family signal transduction pathway is one or more of A83-01, SB-431542, SB-505124, SB-525334, LY364947, SC-203294, SD-208, and SJN2511;

wherein the inhibitor of a BMP signal transduction pathway is one or more of chordin, noggin, follistatin, dorsomorphin, DMH1 and LDN193189; and wherein the GSK-3β inhibitor is at least one of CHIR99021, kenpaullone, and 6-bromoindirubin-3'-oxime.

6. The method of claim 1, wherein the first culture media comprises dorsomorphin and A83-01, and the second culture media comprises CHIR99021, SB-431542, and the extracellular matrix.

* * * * *

SEQUENCE LISTING

<160> NUMBER OF SEQ ID NOS: 5

<210> SEQ ID NO 1
<211> LENGTH: 22
<212> TYPE: DNA
<213> ORGANISM: Homo sapiens

<400> SEQUENCE: 1
ctcgcatggt cagtaaaagc aa 22

<210> SEQ ID NO 2
<211> LENGTH: 22
<212> TYPE: DNA
<213> ORGANISM: Homo sapiens

<400> SEQUENCE: 2
gggtttttgc tggaatcctg gt 22

<210> SEQ ID NO 3
<211> LENGTH: 20
<212> TYPE: DNA
<213> ORGANISM: Homo sapiens

<400> SEQUENCE: 3
ccaagtgtgg ctcaaaggat 20

<210> SEQ ID NO 4
<211> LENGTH: 20
<212> TYPE: DNA
<213> ORGANISM: Homo sapiens

<400> SEQUENCE: 4
cccaatcttc gactggactc 20

<210> SEQ ID NO 5
<211> LENGTH: 140
<212> TYPE: PRT
<213> ORGANISM: Homo sapiens

<400> SEQUENCE: 5

```
Ser Arg Leu Gln Thr Ala Pro Val Pro Met Pro Asp Leu Lys Asn Val
1               5                   10                  15

Lys Ser Lys Ile Gly Ser Thr Glu Asn Leu Lys His Gln Pro Gly Gly
            20                  25                  30
```

-continued

```
Gly Lys Val Gln Ile Ile Asn Lys Lys Leu Asp Leu Ser Asn Val Gln
        35                  40                  45

Ser Lys Cys Gly Ser Lys Asp Asn Ile Lys His Val Leu Gly Gly Gly
    50                  55                  60

Ser Val Gln Ile Val Tyr Lys Pro Val Asp Leu Ser Lys Val Thr Ser
65                  70                  75                  80

Lys Cys Gly Ser Leu Gly Asn Ile His His Lys Pro Gly Gly Gly Gln
                85                  90                  95

Val Glu Val Lys Ser Glu Lys Leu Asp Phe Lys Asp Arg Val Gln Ser
            100                 105                 110

Lys Ile Gly Ser Leu Asp Asn Ile Thr His Val Pro Gly Gly Gly Asn
        115                 120                 125

Lys Lys Ile Glu Thr His Lys Leu Thr Phe Arg Glu
    130                 135                 140
```